(12) United States Patent
DaCosta et al.

(10) Patent No.: US 10,980,583 B2
(45) Date of Patent: Apr. 20, 2021

(54) BONE PLATES, SYSTEMS, AND METHODS OF USE

(71) Applicant: Paragon 28, Inc., Englewood, CO (US)

(72) Inventors: Albert DaCosta, Lone Tree, CO (US); Eric Lintula, Parker, CO (US); Spanky Raymond, Uniontown, OH (US); Frank Bono, Castle Rock, CO (US)

(73) Assignee: PARAGON 28, INC., Englewood, CO (US)

( * ) Notice: Subject to any disclaimer, the term of this patent is extended or adjusted under 35 U.S.C. 154(b) by 405 days.

(21) Appl. No.: 15/668,856

(22) Filed: Aug. 4, 2017

(65) Prior Publication Data

US 2017/0325859 A1    Nov. 16, 2017

Related U.S. Application Data

(63) Continuation of application No. PCT/US2016/016786, filed on Feb. 5, 2016, which is a continuation-in-part of application No. 29/535,566, filed on Aug. 7, 2015, now Pat. No. Des. 819,209.

(60) Provisional application No. 62/112,329, filed on Feb. 5, 2015.

(51) Int. Cl.
*A61B 17/80* (2006.01)

(52) U.S. Cl.
CPC ...... *A61B 17/8057* (2013.01); *A61B 17/8004* (2013.01); *A61B 17/809* (2013.01); *A61B 17/8061* (2013.01)

(58) Field of Classification Search
CPC .............. A61B 17/809; A61B 17/8014; A61B 17/8061; A61B 17/80
See application file for complete search history.

(56) References Cited

U.S. PATENT DOCUMENTS

| | | | |
|---|---|---|---|
| 6,623,486 B1 * | 9/2003 | Weaver | A61B 17/8057 606/281 |
| 8,366,751 B2 * | 2/2013 | Pfefferle | A61B 17/8071 606/286 |
| 9,333,013 B2 | 5/2016 | Prandi et al. | |

(Continued)

OTHER PUBLICATIONS

Extended European Search Report issued in European Patent Application No. 16747336.2 dated Sep. 24, 2018.

(Continued)

*Primary Examiner* — David W Bates
(74) *Attorney, Agent, or Firm* — Heslin Rothenberg Farley & Mesiti P.C.; Jacquelyn A. Graff, Esq.

(57) ABSTRACT

The present invention discloses bone plates, bone plate systems, and methods of using the bone plates. The bone plate includes at least one protuberance at a first end, a first projection at a second end, a second projection at the second end adjacent to the first projection, and a coupling segment positioned between the first and second projections. The bone plate system includes a bone plate and at least one fastener. The bone plate includes at least one tab at a first end, a second end with a first projection and a second projection adjacent to the first projection, and a coupling segment positioned between the first and second projections. The at least one fastener including at least one first fastener for coupling to the at least one tab and a second fastener for coupling to the coupling segment. Methods of using the bone plates is also disclosed.

19 Claims, 35 Drawing Sheets

(56) References Cited

U.S. PATENT DOCUMENTS

| | | | |
|---|---|---|---|
| 9,814,505 B2* | 11/2017 | Leemrijse | A61B 17/8061 |
| 9,888,949 B2 | 2/2018 | Johnson et al. | |
| D819,209 S * | 5/2018 | DaCosta | D24/155 |
| 2003/0074001 A1* | 4/2003 | Apfelbaum | A61B 17/80 606/71 |
| 2004/0210219 A1 | 10/2004 | Bray | |
| 2005/0165400 A1 | 7/2005 | Fernandez | |
| 2006/0142767 A1 | 6/2006 | Green et al. | |
| 2007/0233113 A1* | 10/2007 | Kaelblein | A61B 17/809 606/71 |
| 2008/0114361 A1 | 5/2008 | Butler et al. | |
| 2008/0140130 A1* | 6/2008 | Chan | A61B 17/1728 606/280 |
| 2008/0234749 A1 | 9/2008 | Forstein | |
| 2010/0274293 A1 | 10/2010 | Terrill et al. | |
| 2010/0312285 A1 | 12/2010 | White et al. | |
| 2011/0009866 A1* | 1/2011 | Johnson | A61B 17/8052 606/70 |
| 2011/0295324 A1 | 12/2011 | Donley et al. | |
| 2012/0209334 A1* | 8/2012 | Lewis | A61B 17/8061 606/286 |
| 2014/0066995 A1* | 3/2014 | McCormick | A61B 17/809 606/281 |
| 2014/0148859 A1 | 5/2014 | Taylor et al. | |
| 2015/0045837 A1* | 2/2015 | Parekh | A61B 17/8014 606/281 |
| 2016/0324532 A1* | 11/2016 | Montoya | A61B 17/1728 |
| 2019/0307570 A1* | 10/2019 | Boyer | A61B 17/80 |

OTHER PUBLICATIONS

International Search Report and Written Opinion issued in PCT Application PCT/US2016/016786 dated Apr. 14, 2016.

Extended European Search Report issued in corresponding European Patent Application No. EP 19168648.4 dated Jul. 19, 2019.

* cited by examiner

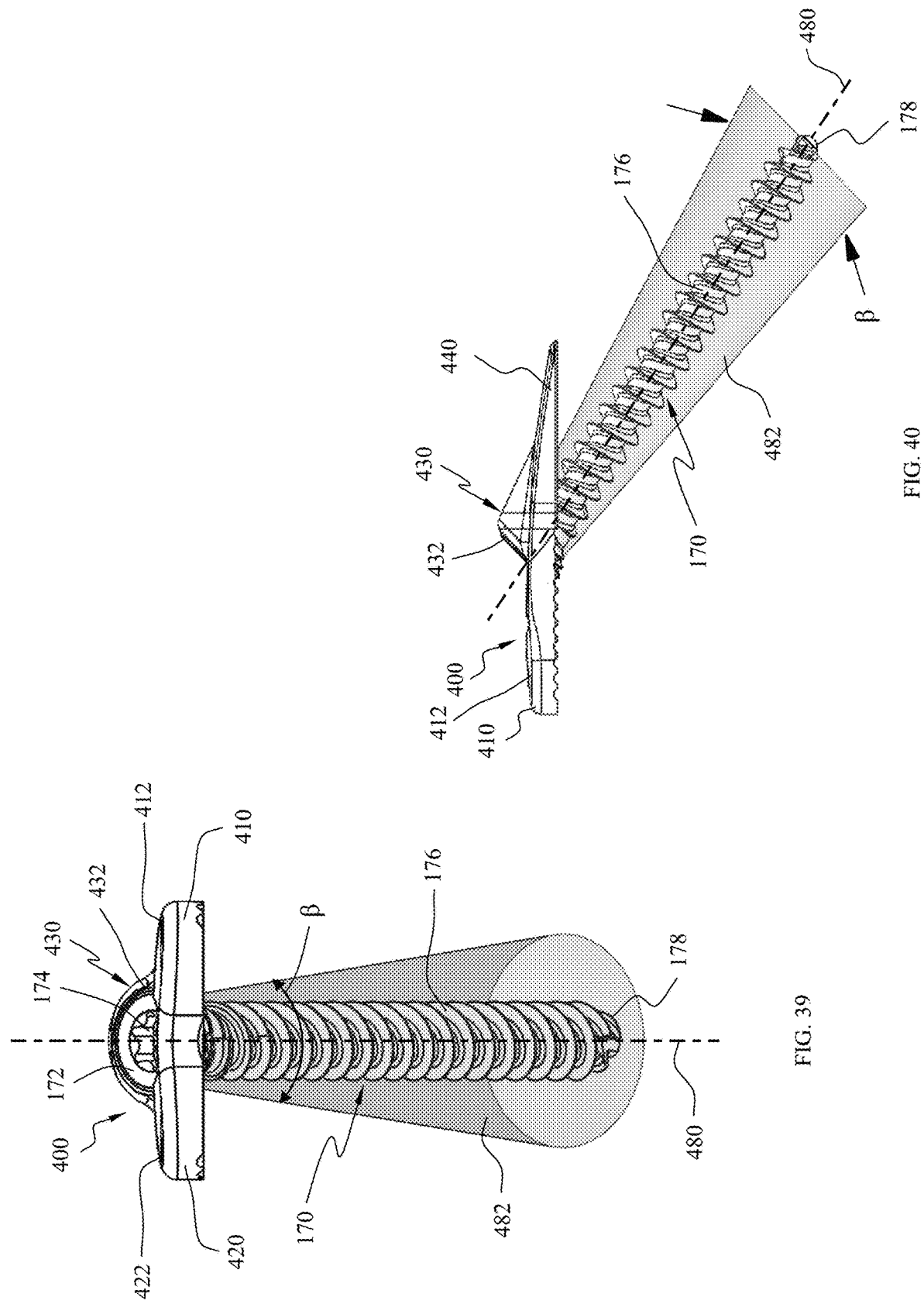

BONE PLATES, SYSTEMS, AND METHODS OF USE

CROSS-REFERENCE TO RELATED APPLICATION

This application is a continuation of PCT Application No. PCT/US2016/016786 filed on Feb. 5, 2016, which claims the priority benefit under 35 U.S.C. § 119(e) from U.S. provisional patent application No. 62/112,329 filed Feb. 5, 2015 and from U.S. design patent application No. 29/535,566 filed Aug. 7, 2015, each of which are incorporated herein by reference in their entireties.

FIELD OF THE INVENTION

The present invention relates generally to the field of orthopedics related to orthopedic bone plates, specifically, bone plates, systems, and methods for using the bone plates.

SUMMARY OF THE INVENTION

The present invention is directed toward bone plates, bone plate systems, and methods of using the bone plates.

In one aspect, provided herein is a bone plate. The bone plate may include, for example, at least one protuberance at a first end, a first projection at a second end, a second projection at the second end adjacent to the first projection, and a coupling segment positioned between the first projection and the second projection.

In another aspect, provided herein is a bone plate system including, for example, a bone plate and at least one fastener. The bone plate including at least one tab at a first end, a second end with a first projection and a second projection adjacent to the first projection, and a coupling segment positioned between the first projection and the second projection. The at least one fastener including at least one first fastener for coupling to the at least one tab and a second fastener for coupling to the coupling segment.

In yet another aspect, provided herein is a method for using the bone plate. The method including, for example, cutting an incision over a patient's bone and preparing the patient's bone. The method also including selecting a bone plate and inserting a second end of the bone plate into a second bone portion. The method further including aligning the bone plate on a first bone portion and inserting at least one fastener through the bone plate and into the first bone portion. The method also including inserting a fastener through the bone plate and into the second bone portion and closing the incision.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 39 is a first end view of the bone plate of FIG. 30 with a central fastener showing the insertion angles for the fastener, in accordance with an aspect of the present invention;

FIG. 40 is another side view of the bone plate and fastener of FIG. 39 showing the insertion angles for the central fastener, in accordance with an aspect of the present invention;

DETAILED DESCRIPTION FOR CARRYING OUT THE INVENTION

Generally stated, disclosed herein are bone plates. The terms "bone plate," "implant," and "plate" may be used interchangeably herein as they essentially refer to the same device. Further, bone plate systems and methods for using the bone plate systems are discussed.

In this detailed description and the following claims, the words proximal, distal, anterior, posterior, medial, lateral, superior, inferior, dorsal and plantar are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Figure 1:
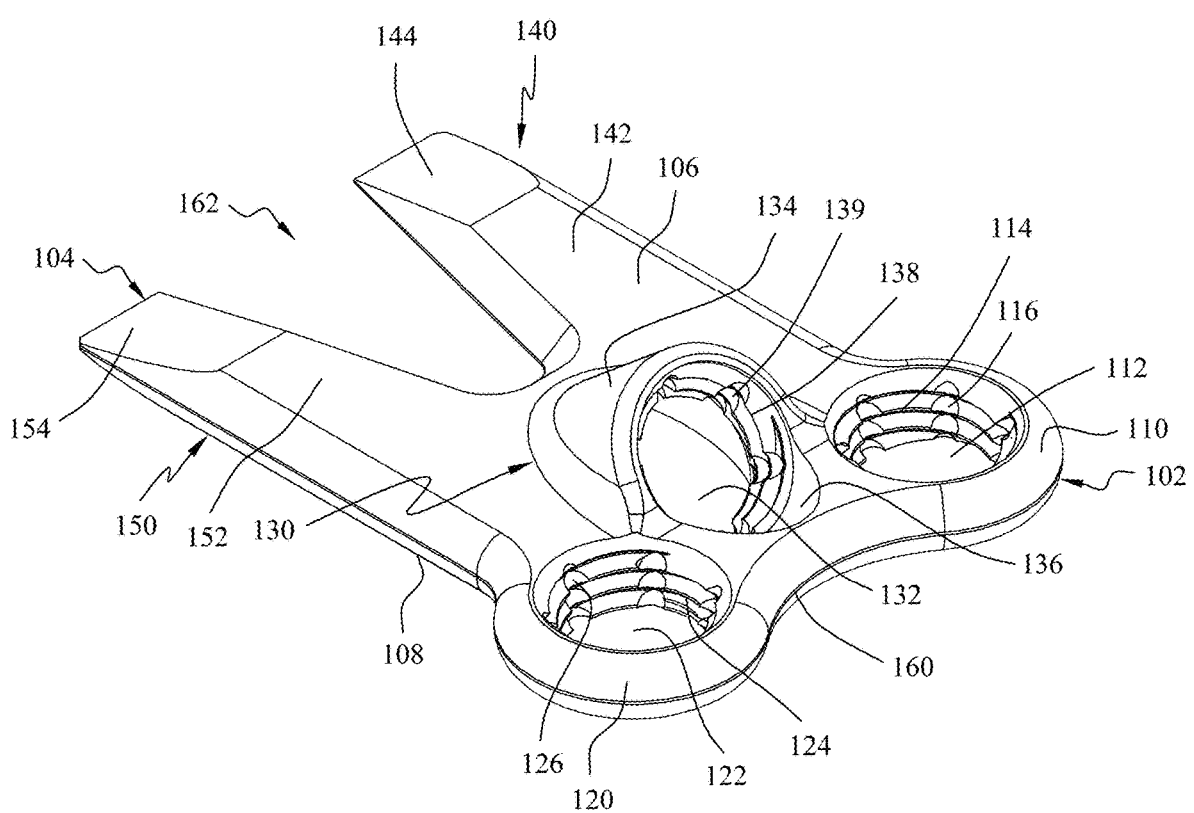
FIG. 1 is a top perspective view of a bone plate, in accordance with an aspect of the present invention.
Figure 2:
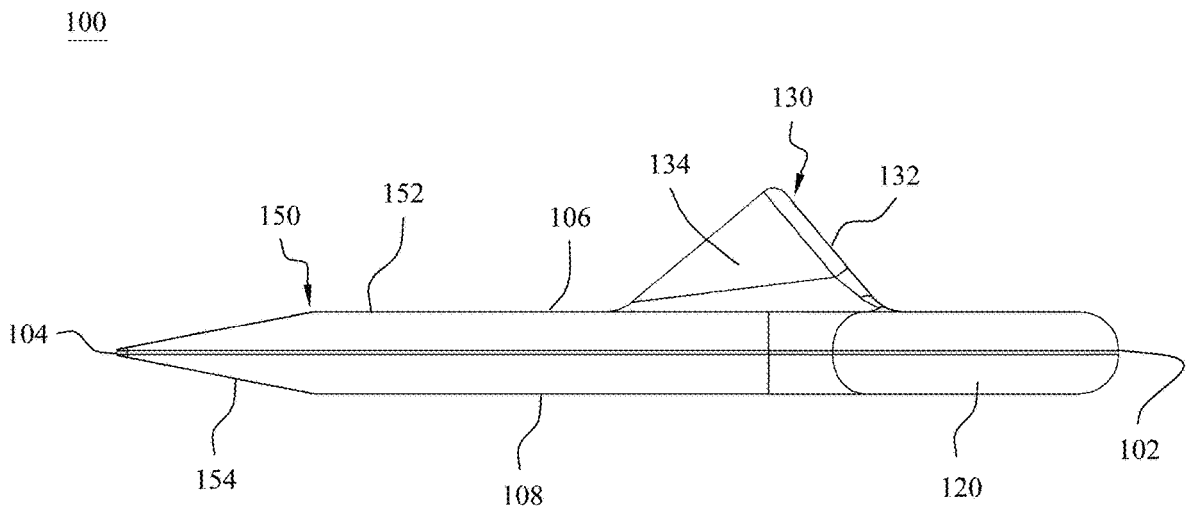
FIG. 2 is a side view of the bone plate of FIG. 1, in accordance with an aspect of the present invention.
Figure 3:
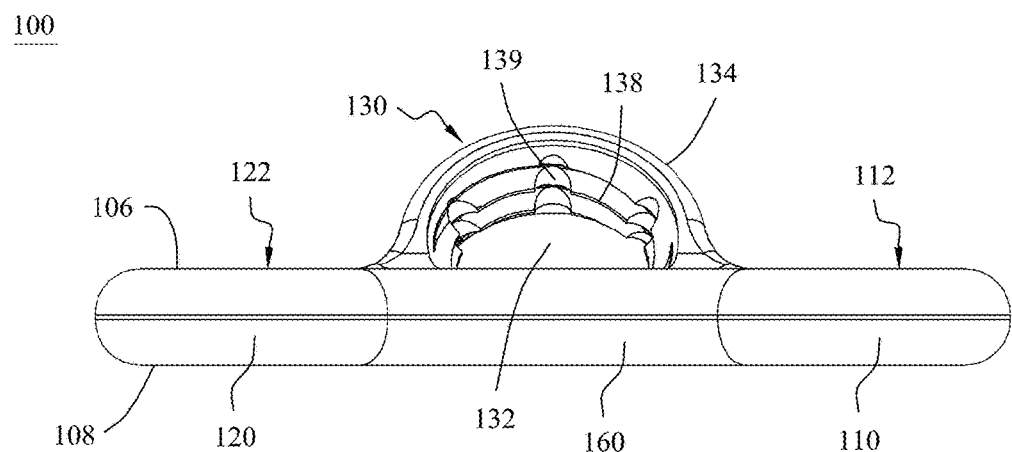
FIG. 3 is a first end view of the bone plate of FIG. 1, in accordance with an aspect of the present invention.
Figure 4:
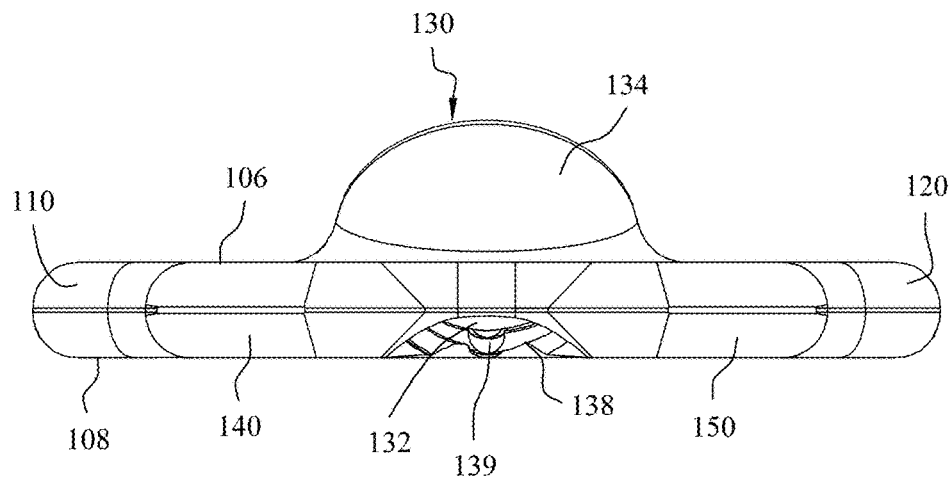
FIG. 4 is a second end view of the bone plate of FIG. 1, in accordance with an aspect of the present invention.

Referring to the drawings, wherein like reference numerals are used to indicate like or analogous components throughout the several views, and with particular reference to FIGS. 1-7, a bone plate 100 is shown. As shown in FIG. 1, the bone plate 100 may have a first end 102, a second end 104 opposite the first end 102, a top surface 106, and a bottom surface 108 opposite the top surface 106. The first end 102 may include, for example, at least one first lobe 110, at least one second lobe 120, and a coupling segment 130. The second end 104 may include, for example, a first projection 140 and a second projection 150. The plate 100 may also optionally include a recessed or curved portion 160 positioned between the first and second lobes 110, 120.

As shown in FIGS. 1 and 5-8, the at least one first lobe, fastener opening portion, portion, extension portion, ear, protuberance, enlarged aspect, or tab 110 may be one lobe 110. The first lobe, fastener opening portion, portion, extension portion, ear, protuberance, enlarged aspect, or tab 110 may include an opening 112 extending through the bone plate 100 from the top surface 106 to the bottom surface 108. The first lobe 110 may further include a threaded portion 114 on the interior surface of the opening 112. The threaded portion 114 may have, for example, at least one scallop or cutout 116 forming a break in the threads of the threaded portion 114. The threaded portion 114 may be, for example, a screw hole for receiving a fastener or screw. The threaded portion 114 and at least one cutout 116 are shaped to lock the fastener or screw in the opening 112. It is also contemplated that the lobe 110 may be, for example, multiple lobes 110 to provide for additional fastening locations to secure the plate 100 to the patient's bones.

The at least one second lobe, fastener opening portion, portion, extension portion, ear, protuberance, enlarged aspect, or tab 120 may be one lobe 120, as shown in FIGS. 1, 5-6, and 8. The second lobe, fastener opening portion, portion, extension portion, ear, protuberance, enlarged aspect, or tab 120 may include an opening 122 extending through the bone plate 100 from the top surface 106 to the bottom surface 108. The second lobe 120 may further include a threaded portion 124 on the interior surface of the opening 122. The threaded portion 124 may have, for example, at least one scallop or cutout 126 forming a break in the threads of the threaded portion 124. The threaded portion 124 may be, for example, a screw hole for receiving a fastener or screw. The threaded portion 124 and at least one cutout 126 are shaped to lock the fastener or screw in the opening 122. It is also contemplated that the at least one lobe 120 may be, for example, multiple lobes 120 to provide for additional fastening locations to secure the plate 100 to the patient's bones.

The first lobe 110 may be, for example, aligned with or offset from the second lobe 120. Alternative numbers of lobes 110, 120 are also contemplated to provide for additional fastening locations for securing the plate 100 to the patient's bones.

Figure 5:
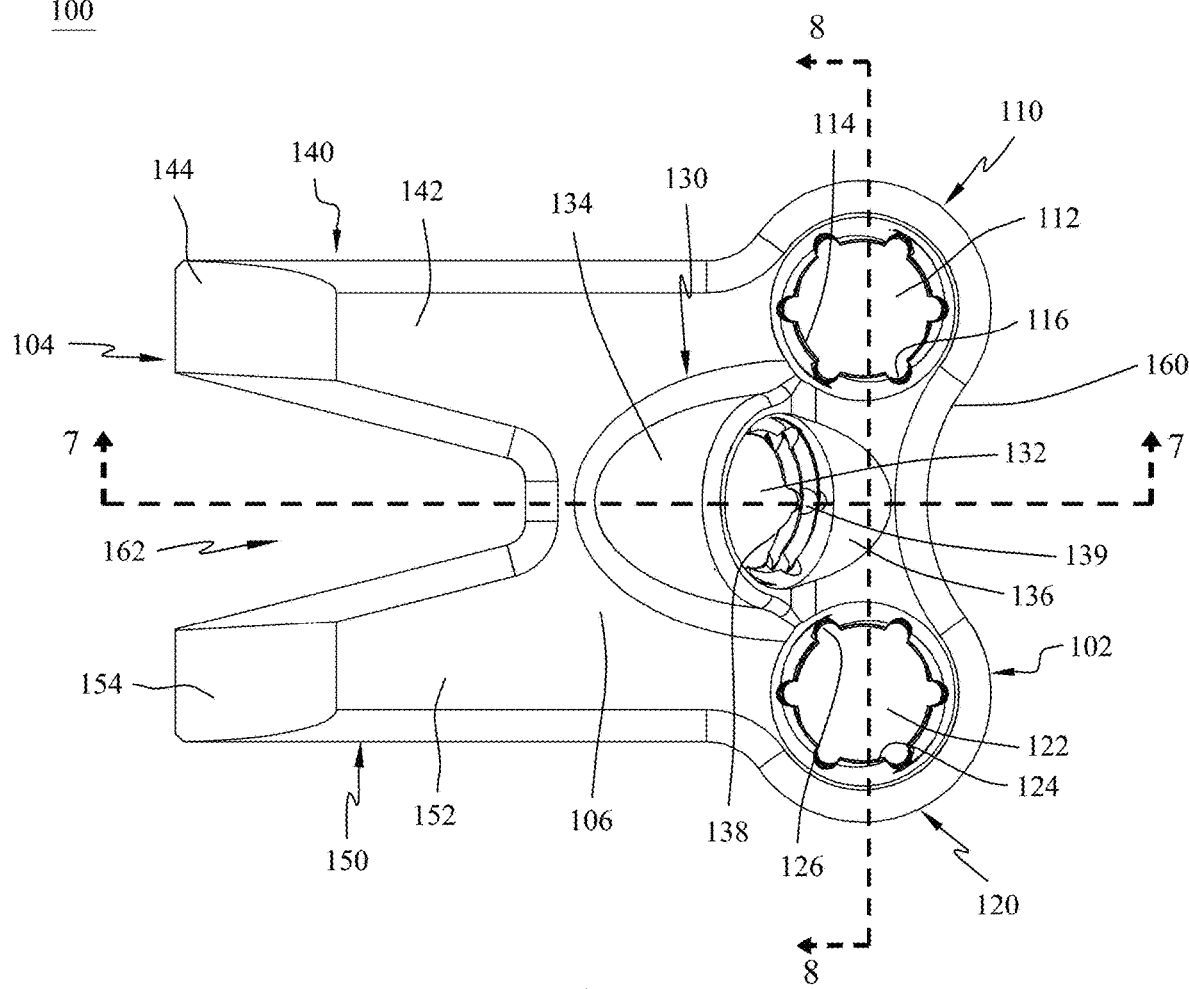
FIG. 5 is a top view of the bone plate of FIG. 1, in accordance with an aspect of the present invention.
Figure 6:
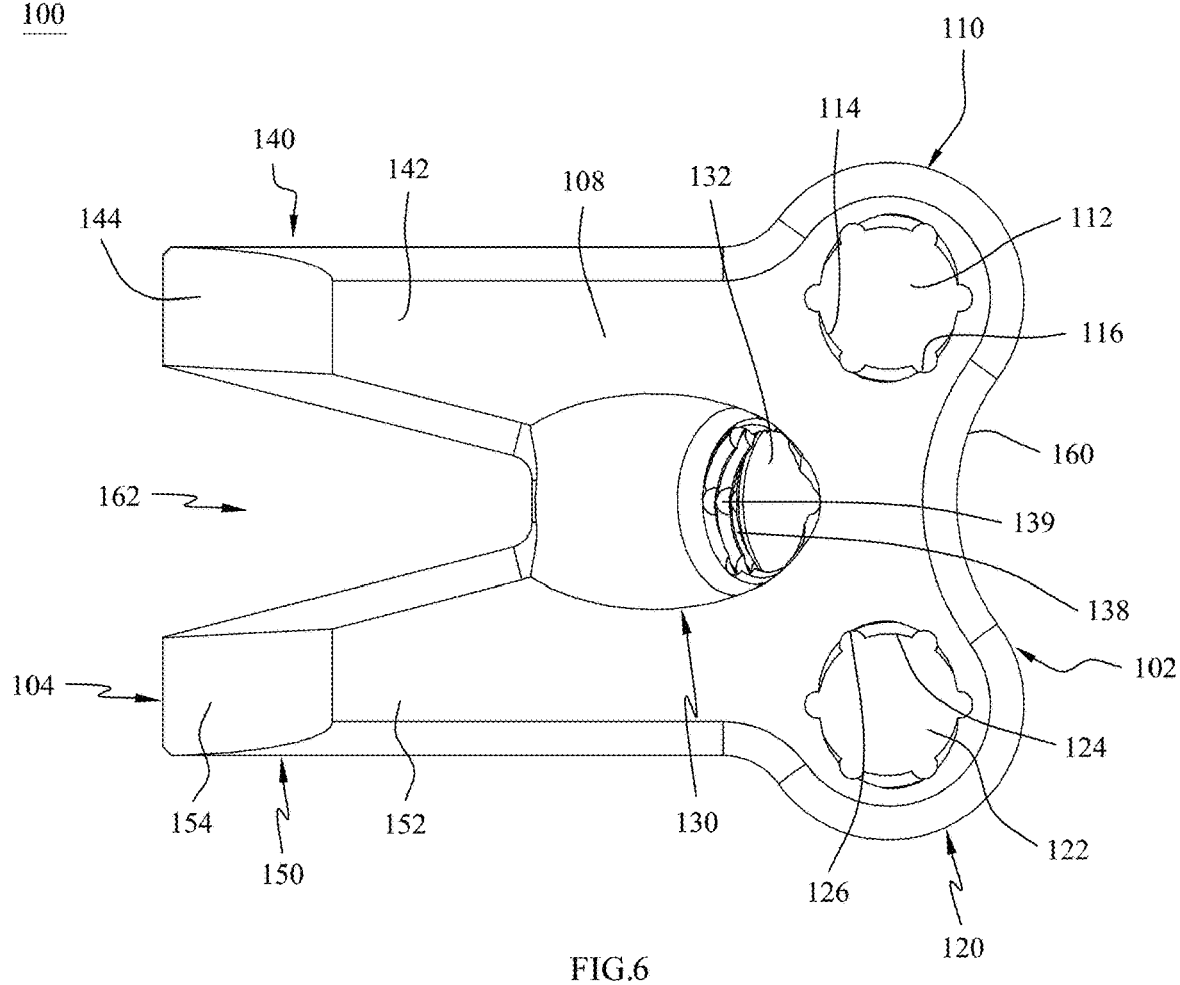
FIG. 6 is a bottom view of the bone plate of FIG. 1, in accordance with an aspect of the present invention.
Figure 7:
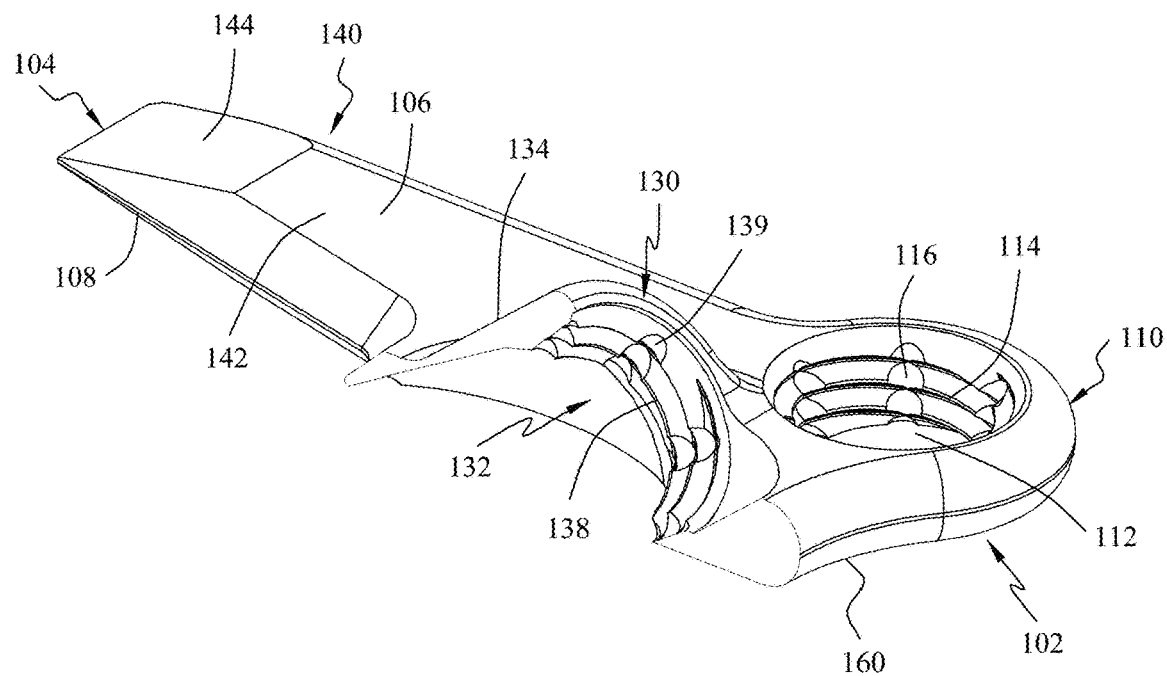
FIG. 7 is a perspective view of a cross-section of the bone plate of FIG. 1 taken along line 7-7 in FIG. 5, in accordance with an aspect of the present invention.
Figure 8:
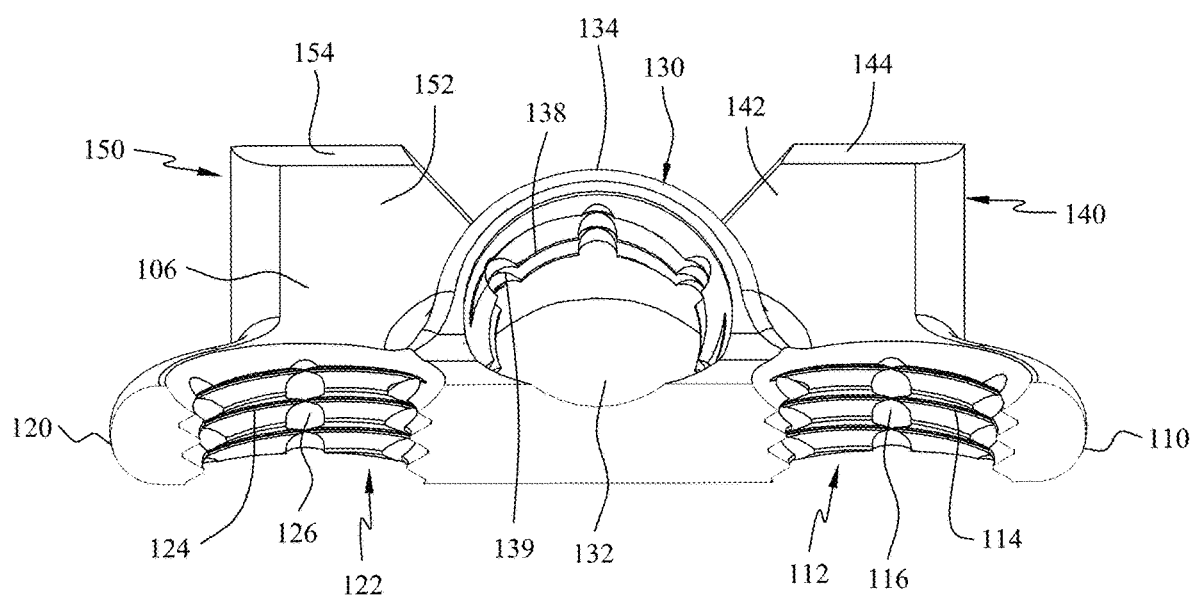
FIG. 8 is a perspective view of a cross-section of the bone plate of FIG. 1 taken along line 8-8 in FIG. 5, in accordance with an aspect of the present invention.
Figure 9:
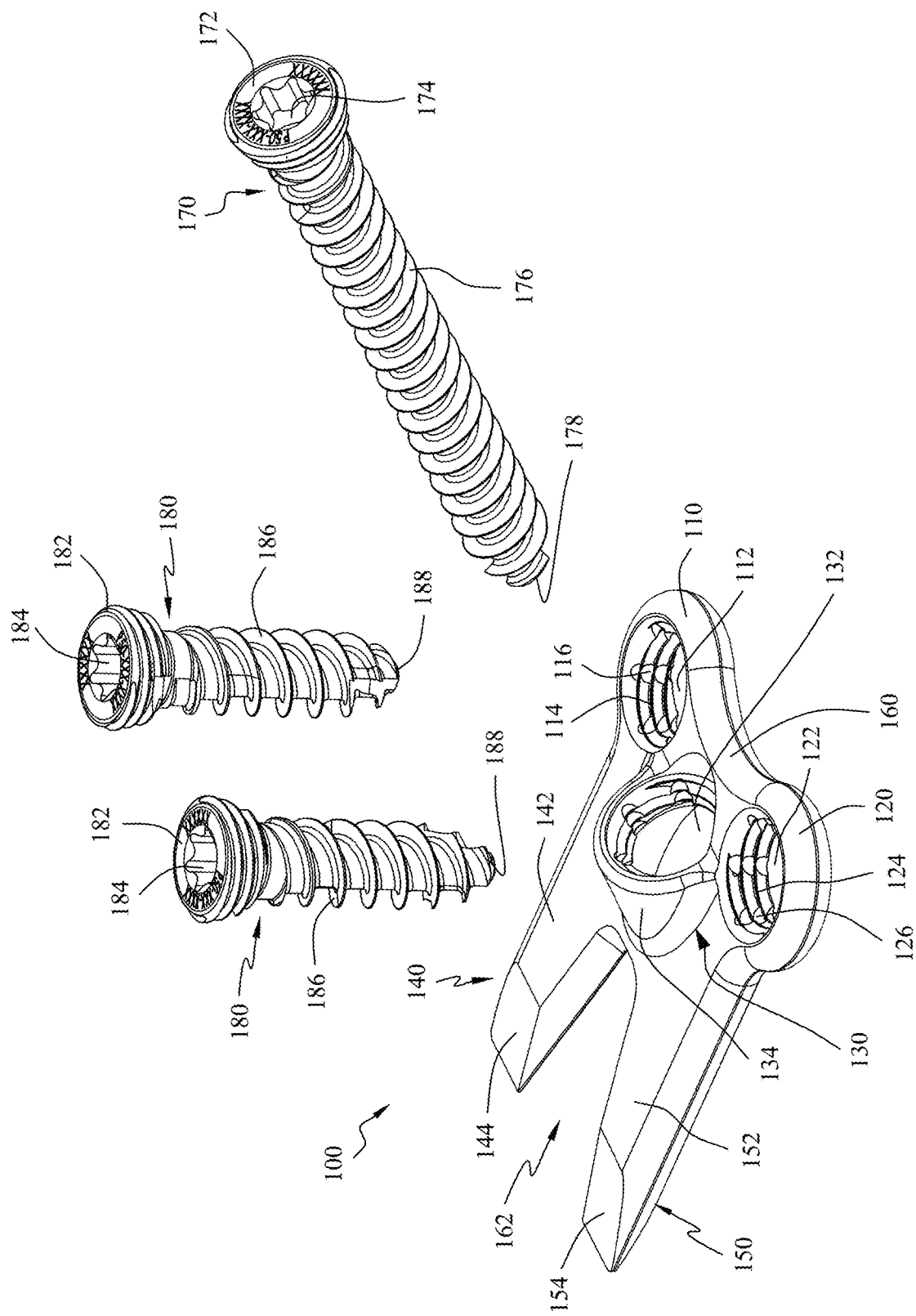
FIG. 9 is an exploded perspective view of the bone plate of FIG. 1 and three fasteners, in accordance with an aspect of the present invention.
Figure 10:
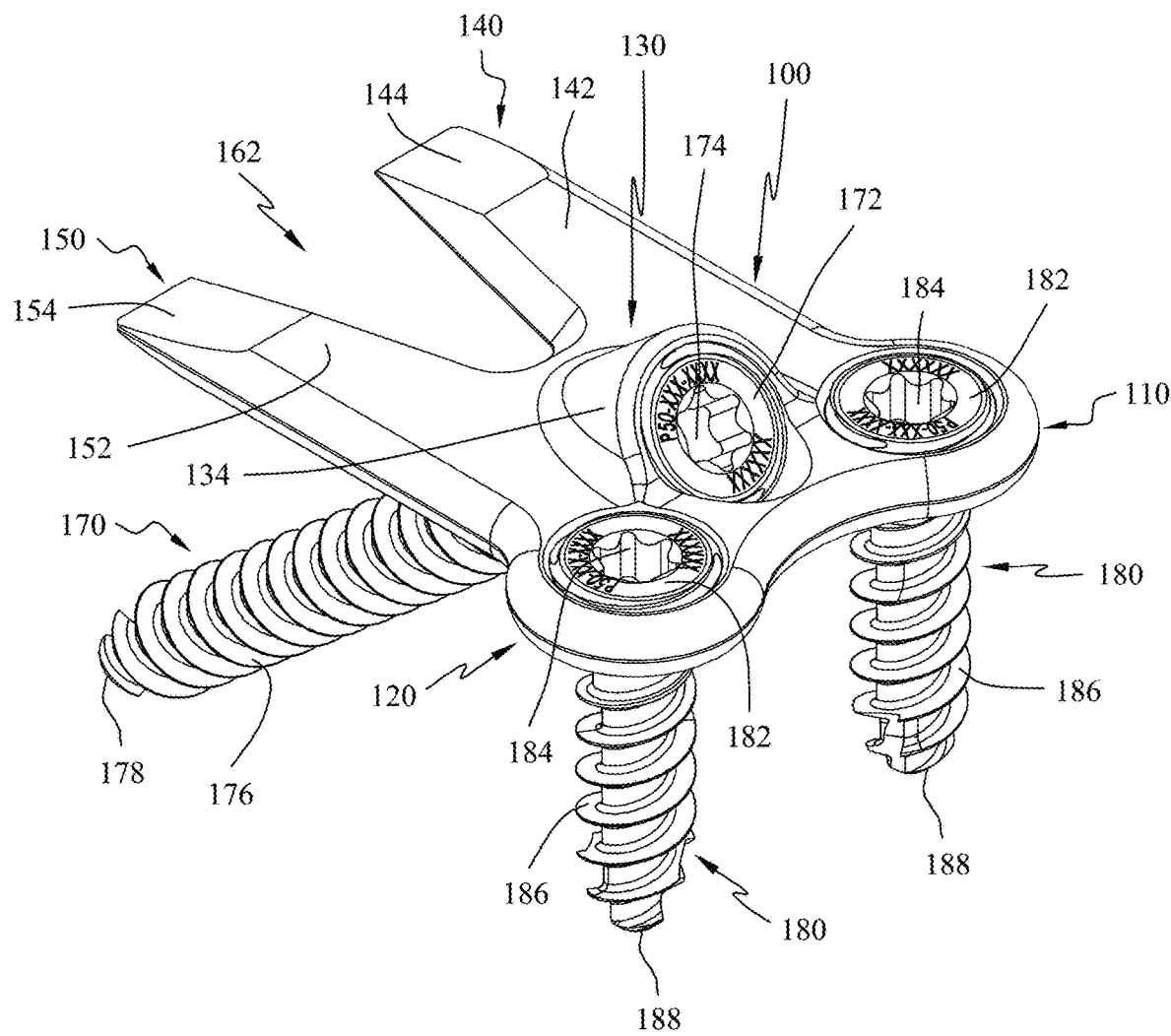
FIG. 10 is a top perspective view of a bone plate system including the fasteners of FIG. 8 inserted into the bone plate of FIG. 1, in accordance with an aspect of the present invention.
Figure 11:
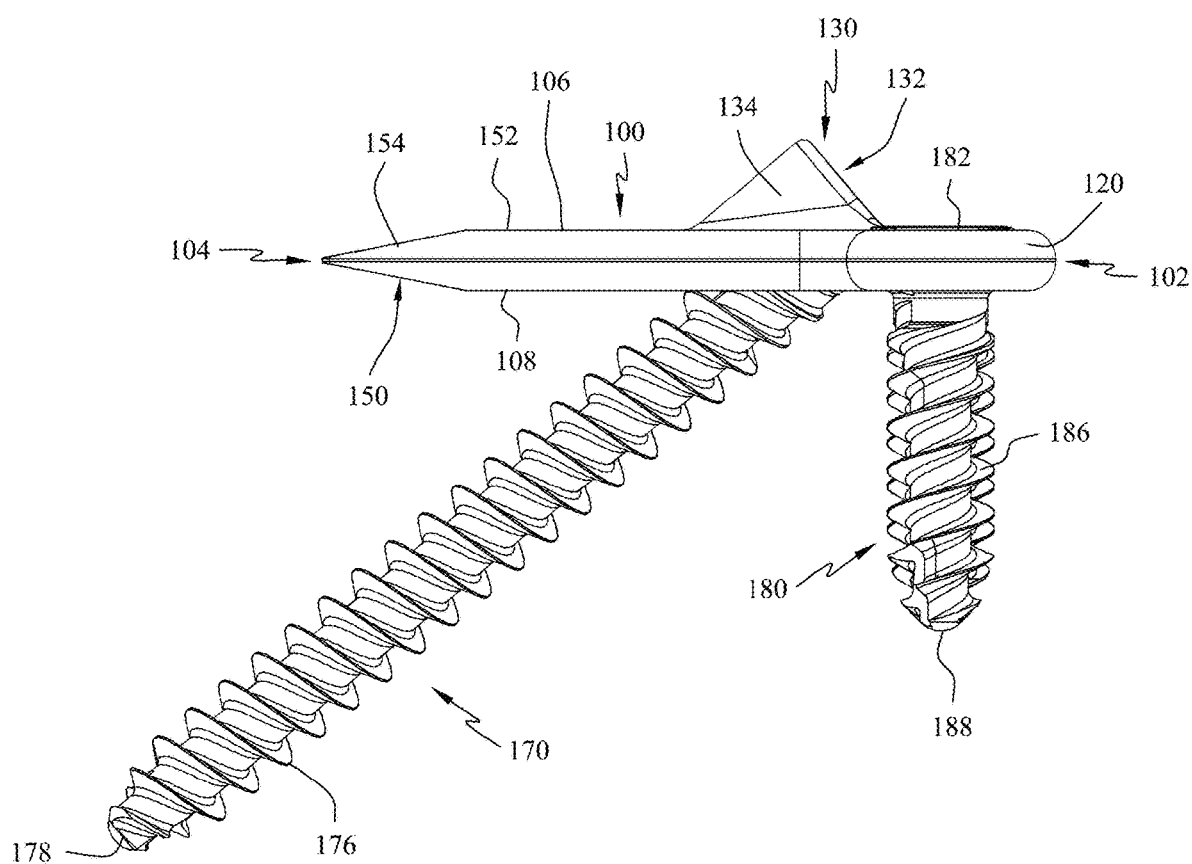
FIG. 11 is a side view of the bone plate system of FIG. 9, in accordance with an aspect of the present invention.
Figure 12:
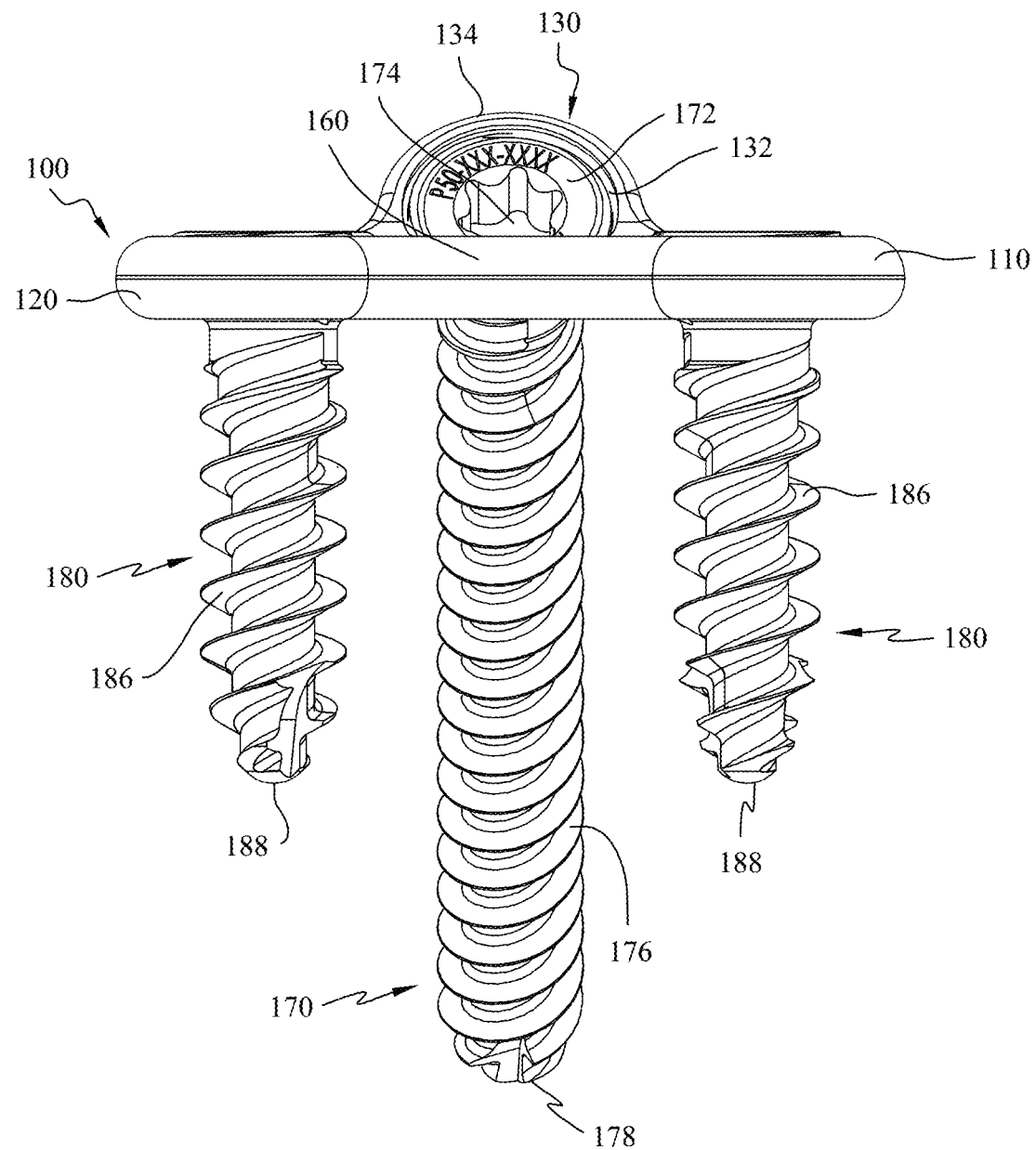
FIG. 12 is a first end view of the bone plate system of FIG. 9, in accordance with an aspect of the present invention.
Figure 13:
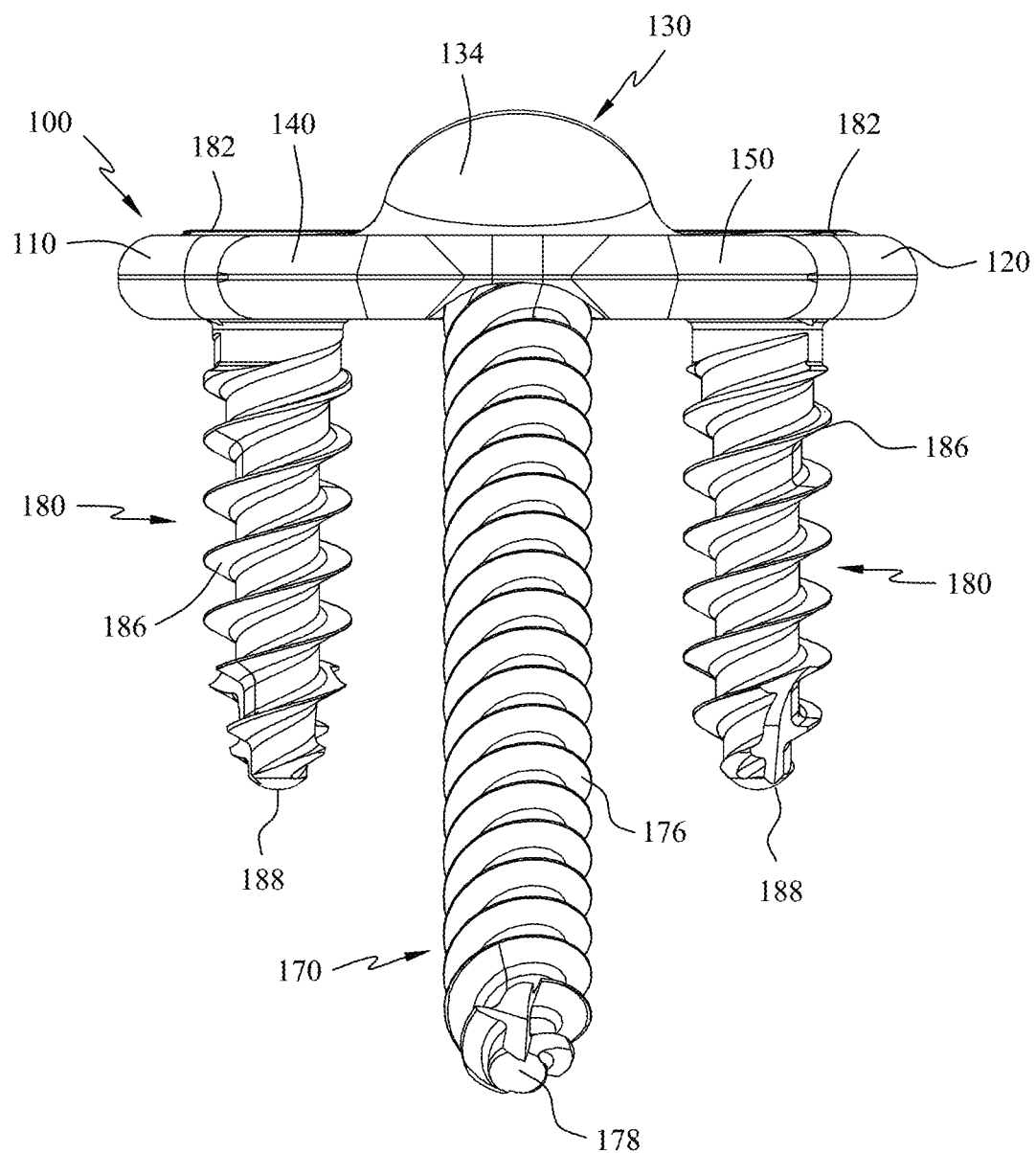
FIG. 13 is a second end view of the bone plate system of FIG. 9, in accordance with an aspect of the present invention.
Figure 14:
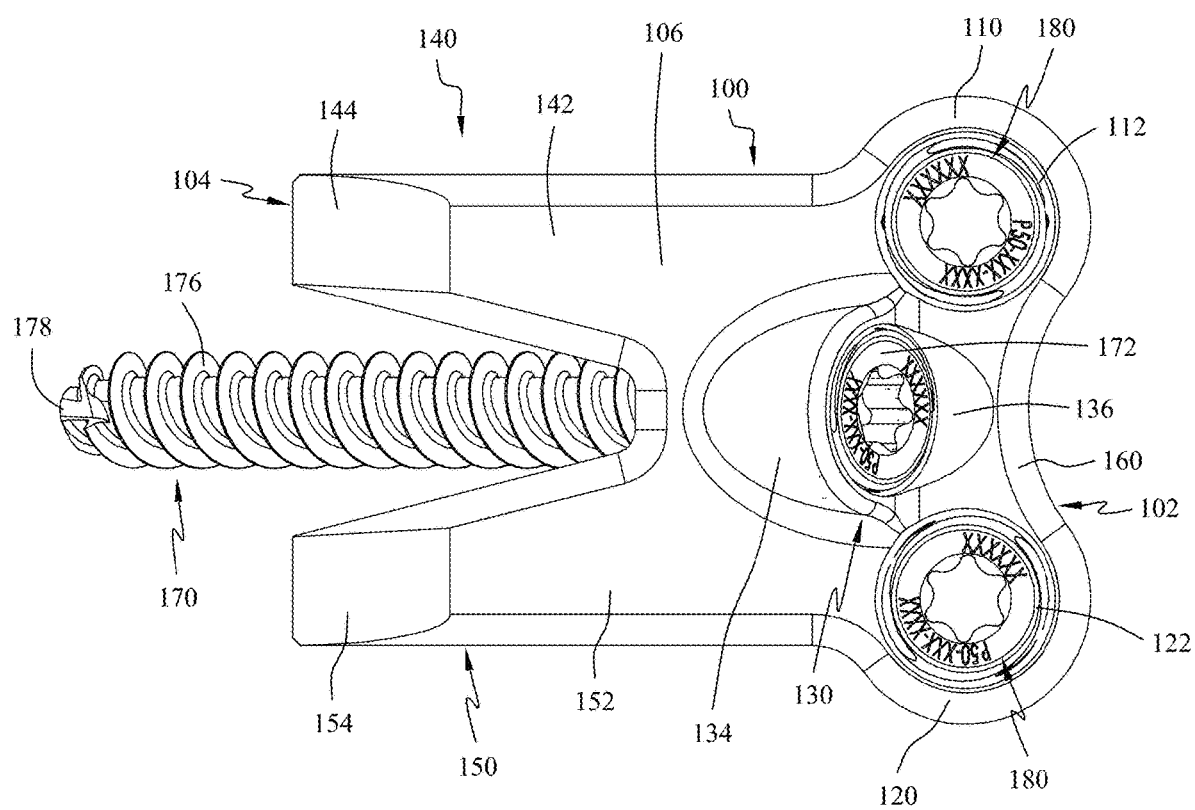
FIG. 14 is a top view of the bone plate system of FIG. 9, in accordance with an aspect of the present invention.
Figure 15:
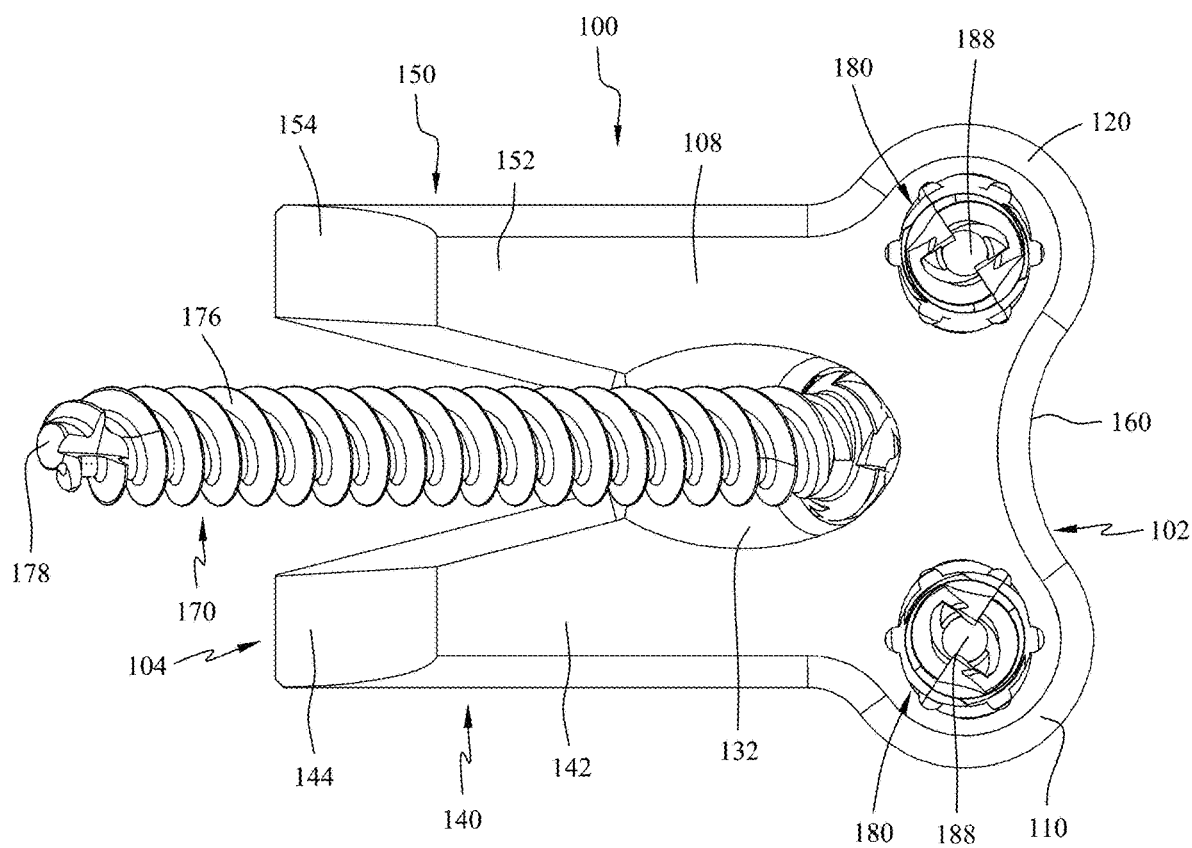
FIG. 15 is a bottom view of the bone plate system of FIG. 9, in accordance with an aspect of the present invention.
Figure 16:
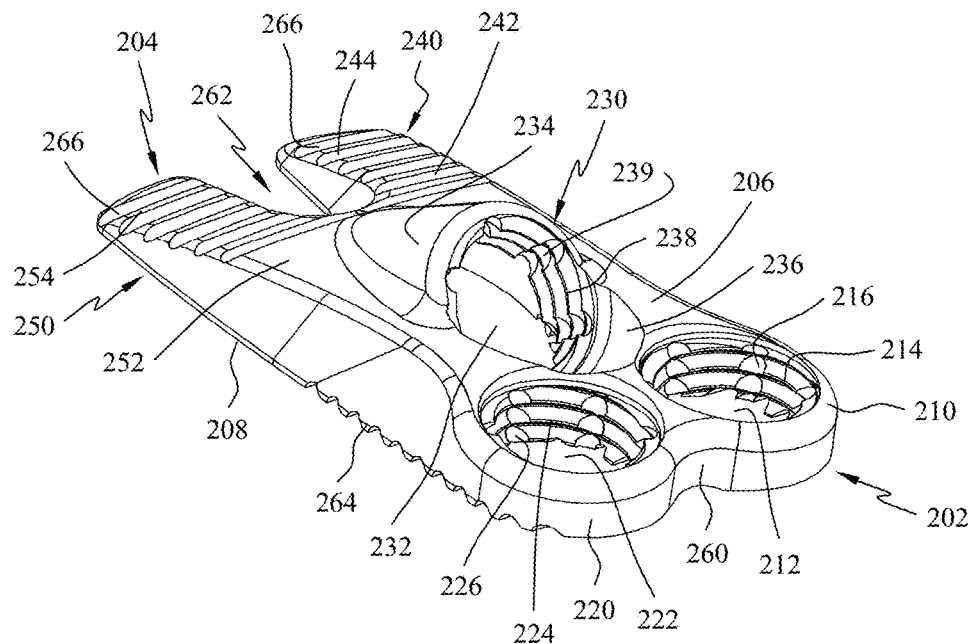
FIG. 16 is a top perspective view of another bone plate, in accordance with an aspect of the present invention.
Figure 17:
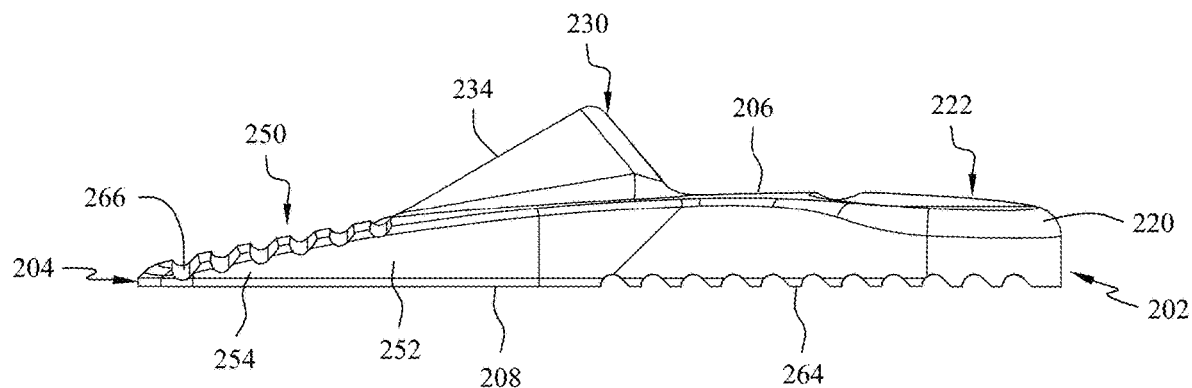
FIG. 17 is a side view of the bone plate of FIG. 16, in accordance with an aspect of the present invention.
Figure 18:
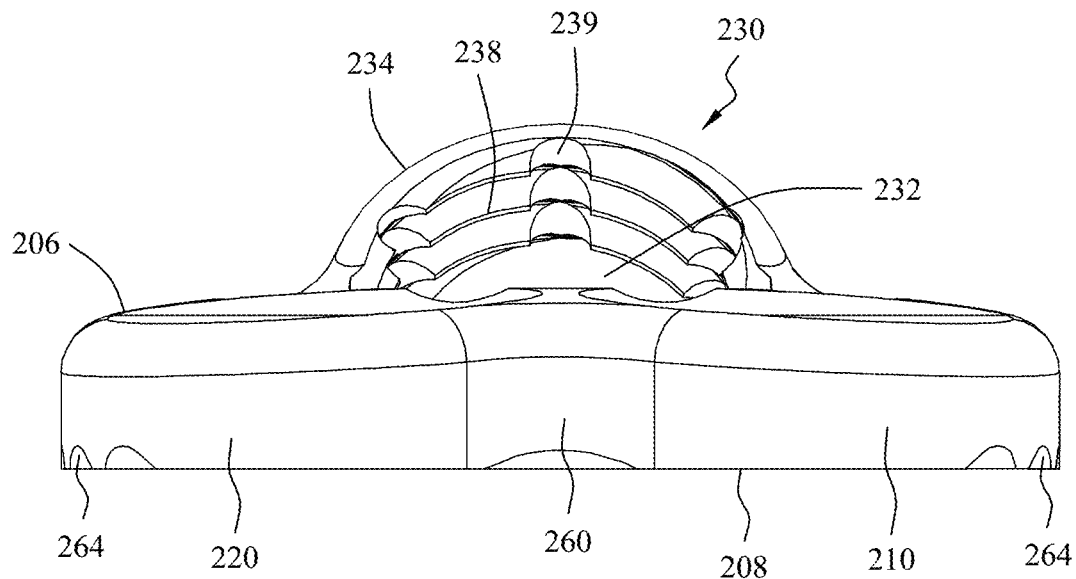
FIG. 18 is a first end view of the bone plate of FIG. 16, in accordance with an aspect of the present invention.
Figure 19:
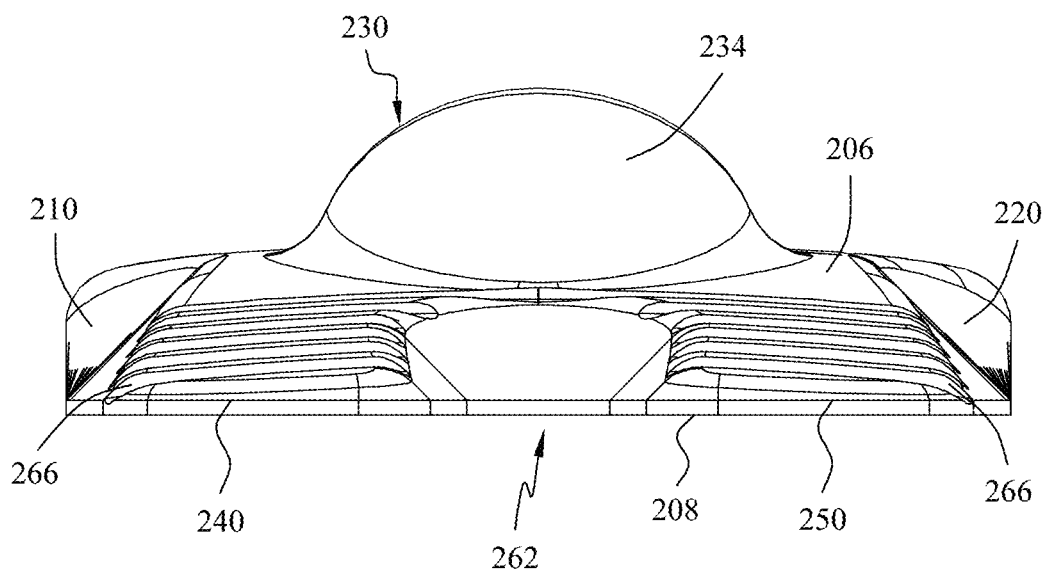
FIG. 19 is a second end view of the bone plate of FIG. 16, in accordance with an aspect of the present invention.
Figure 20:
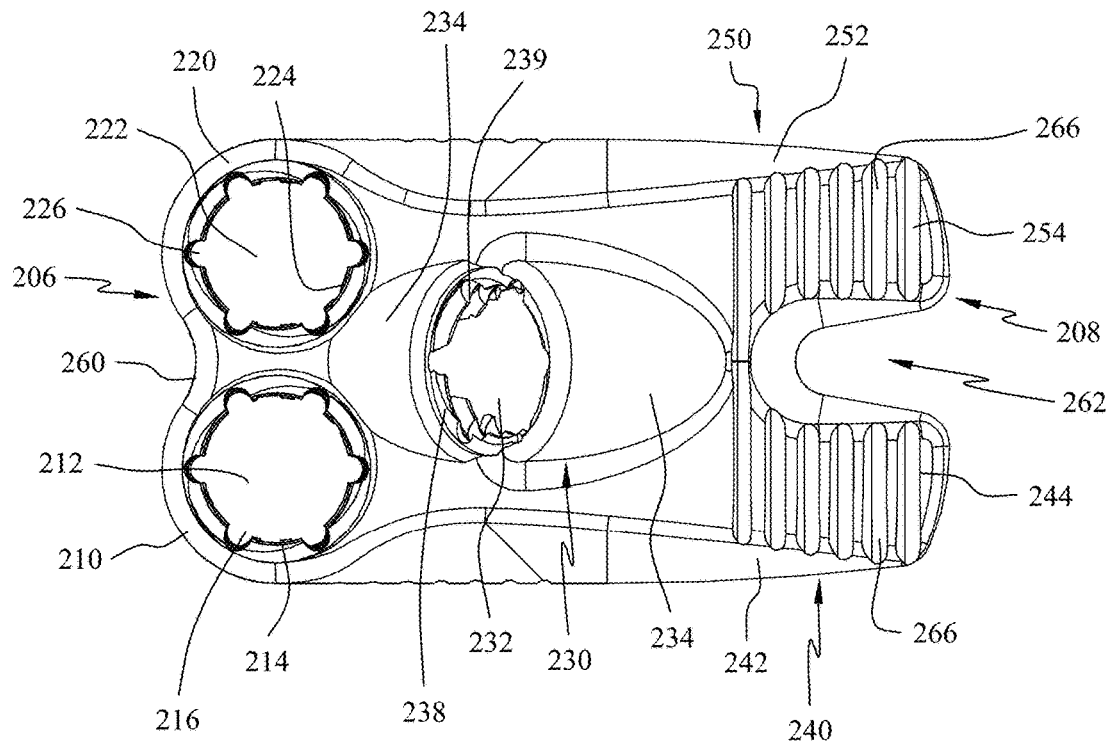
FIG. 20 is a top view of the bone plate of FIG. 16, in accordance with an aspect of the present invention.
Figure 21:
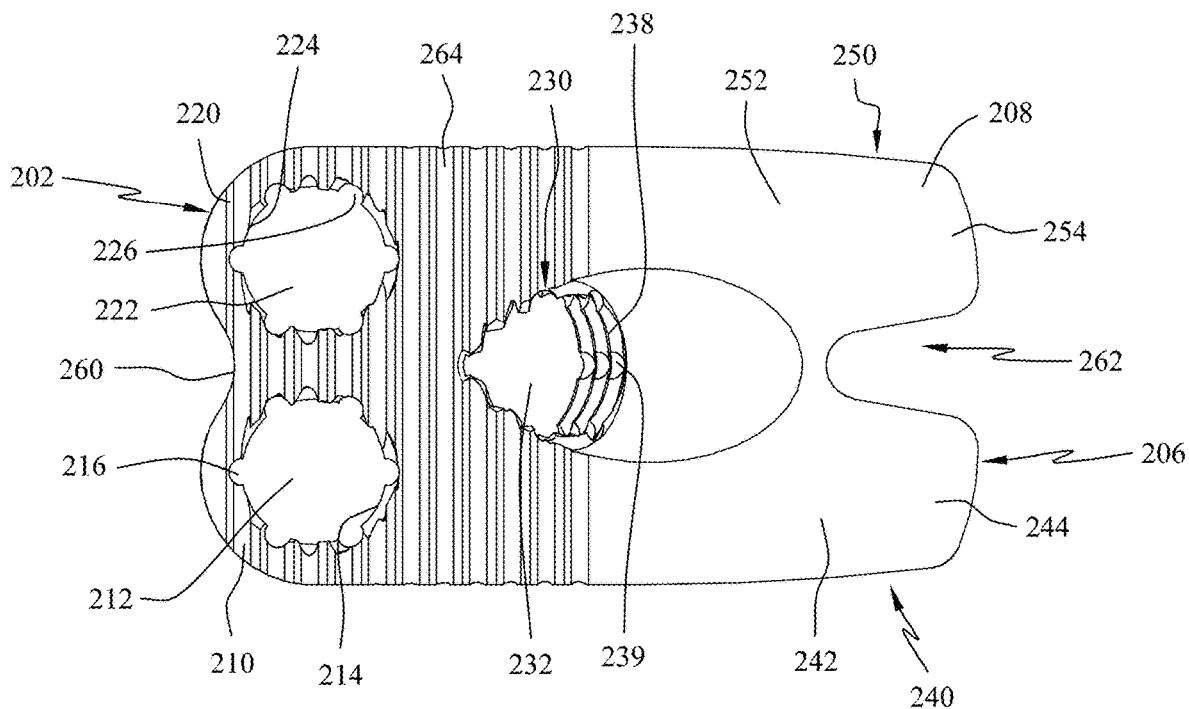
FIG. 21 is a bottom view of the bone plate of FIG. 16, in accordance with an aspect of the present invention.

As shown in FIGS. 1 and 5-9, the coupling segment 130 may include, for example, an opening 132 extending from the top surface 106 through the bottom surface 108 of the plate 100. The opening 132 may be, for example, positioned in-line with or partially recessed into the plate 100. The opening 132 may be positioned, for example, to extend through the plate 100 at an angle. The opening 132 may include a cover or hood portion 134 extending away from the top surface 106 of the plate 100. The opening 132 may also have an indentation or concavity 136 that is recessed into the top surface 106 of the bone plate 100, as shown in FIGS. 1, 5, and 7. The opening 132 may have a counterbore allowing for the head of a fastener to be flush with the opening 132 to avoid irritation to the patient's surrounding tissue after implantation (see FIGS. 12 and 14 for head-hole relationship). Further, the opening 132 may include a threaded portion 138 extending along a portion of the interior surface of the opening 132 from the top surface 106 toward the bottom surface 108, as shown in FIGS. 6 and 7. The threaded portion 138 may have, for example, at least one scallop or cutout 139 forming a break in the threads of the threaded portion 138.

The threaded portions 114, 124, 138 with the cutouts 116, 126, 139 allow for a fastener to be inserted at various angles through the openings 112, 122, 132 and into a patient's bone. The threaded portions 114, 124, 138 allow for fasteners to be inserted and pivoted to the desired orientation in the plate 100 as they are inserted into a patient's bones. The threaded portions 114, 124, 138 provide a surface for the fastener to engage the plate 100 as the fastener passes through the openings 112, 122, 132. In addition, the threaded portions 114, 124, 138 may be, for example, locking threads to secure the fasteners in the desired positions.

As shown in FIGS. 1-2 and 5-7, the first projection 140 may include, for example, a base portion 142 and a tapered portion 144 at the second end 104 of the plate 100. The base portion 142 may extend away from the plate 100 near the coupling segment 130 on a first side of the plate 100. The base portion 142 may have, for example, a generally uniform thickness. The tapered portion 144 may be tapered, for example, from the top surface 106 toward a midpoint between the top surface 106 and the bottom surface 108, from the bottom surface 108 toward the midpoint, or from both the top surface 106 and bottom surface 108 converging at the midpoint. In addition, the tapered portion 144 may be, for example, curved in a superior or inferior direction as it extends away from the base portion 142 of the projection 140. The tapered portion 144 in one embodiment may provide for easier insertion into a patient's bone.

The second projection 150 may include, for example, a base portion 152 and a tapered portion 154 at the second end 104 of the plate 100, as shown in FIGS. 1-2 and 5-6. The base portion 152 may extend away from the plate 100 near the coupling segment 130 on a second side of the plate 100. The base portion 152 may be, for example, a generally uniform thickness. The tapered portion 154 may be tapered, for example, from the top surface 106 to a midpoint between the top surface 106 and the bottom surface 108, from the bottom surface 108 to the midpoint, or from both the top surface 106 and the bottom surface 108 converging at the midpoint. In addition, the tapered portion 154 may be, for example, curved in a superior or inferior direction as it extends away from the base portion 152 of the projection 150. The tapered portion 154 in one embodiment may provide for easier insertion into a patient's bone.

The first projection 140 and second projection 150 may extend slightly away from each other forming a space or channel 162 between the projections 140, 150. The size of the space or channel 162 may be selected to enable insertion of the bone plate 100 into a patient's bone without causing the bone to fracture. For example, the first and second projections 140, 150 may extend away from each other at an angle of approximately 15° to 45° and more preferably at an angle of approximately 25° to 35°, although other angles are also contemplated.

The bone plate 100 may have, for example, a generally uniform thickness from the first end 102 to the second end 104 with the coupling segment 130 extending away from the top surface 106 and the ends 144, 154 being tapered.

The bone plate 100 may be used with fasteners 170, 180 to form a bone plate system, as shown in FIGS. 9-15. The fastener 170 may include, for example, a head 172 and a shaft 176. The head 172 may include a drive opening 174 for coupling to an insertion tool. The shaft 176 may include threads extending from the bottom surface of the head 172 to a tip 178 of the shaft 176. The fasteners 180 may include, for example, a head 182 and a shaft 186. The head 182 may include a drive opening 184 for coupling to an insertion tool. The head 182 may also include threads on the side of the exterior surface. The threads on the head 182 may be configured to engage the threaded portions 114, 124 in the openings 112, 122 in the plate 100 to, for example, lock the fasteners 180 to the plate 100. The shaft 186 may include threads extending from the bottom surface of the head 182 to a tip 188 of the shaft 186. The threads on the shaft 186 may be configured for insertion into a patient's bones. The fasteners 180 may be inserted through the first lobe 110 and the second lobe 120 to engage the threads 114, 124, as shown in FIGS. 10-15. The fastener 170 may be inserted through the opening 132 in the coupling segment 130 to engage the threads 138, as shown in FIGS. 10-15.

As shown in FIGS. 16-22, another bone plate 200 is shown. The bone plate 200 may have first end 202, a second end 204 opposite the first end 202, a top surface 206, and a bottom surface 208 opposite the top surface 206. The first end 202 may include, for example, at least one first lobe 210, at least one second lobe 220, and a coupling segment 230. The second end 204 may include, for example, a first projection 240 and a second projection 250. The first and second projections 240, 250 may be, for example, shorter and wider than the first and second projections 140, 150 of the plate 100. The plate 200 may also optionally include a recessed or curved portion 260 positioned between the first and second lobes 210, 220.

As shown in FIGS. 16 and 20-22, the at least one first lobe, fastener opening portion, portion, extension portion, ear, protuberance, enlarged aspect, or tab 210 may be one lobe 210 including an opening 212 with a threaded portion 214 and at least one scallop or cutout 216. The first lobe 210 may be of the type described above with reference to at least one first lobe 110, which will not be described again here for brevity sake. The at least one second lobe, fastener opening portion, portion, extension portion, ear, protuberance, enlarged aspect, or tab 220 may be one lobe 220 including an opening 222 with a threaded portion 224 and at least one scallop or cutout 226. The second lobe 220 may be of the type described above with reference to the at least one second lobe 120, which will not be described again here for brevity sake.

The coupling segment 230, as shown in FIGS. 16, 18, and 20-21, may include, for example, an opening 232 with a cover or hood portion 234, an indentation or concavity 236, and a threaded portion 238 with at least one cutout or scallop 239. The coupling segment 230 may be of the type described above with reference to the coupling segment 130, which will not be described again here for brevity sake.

As shown in FIGS. 16, 19, 20, and 22, the first projection 240 may include, for example, a base portion 242 and a tapered portion 244 at the second end 204 of the plate 200. The base portion 242 may extend away from the plate 200 near the coupling segment 230 on a first side of the plate 200. The base portion 242 may have, for example, a generally uniform thickness. The tapered portion 244 may be tapered, for example, from the top surface 206 toward a midpoint between the top surface 206 and the bottom surface 208, from the bottom surface 208 toward the midpoint, or from both the top surface 206 and bottom surface 208 converging at the midpoint. In addition, the tapered portion 244 may be, for example, curved in a superior or inferior direction as it extends away from the base portion 242 of the projection 240. The tapered portion 244 in one embodiment may provide for easier insertion into a patient's bone. The top surface 206 of the first projection 240 may have, for example, a plurality of grooves 266 or a like textured surface to increase surface friction between the plate 200 and the patient's bone and to assist with bone ingrowth into the plate 200 and fixation with adjacent bone surfaces.

The second projection 250 may include, for example, a base portion 252 and a tapered portion 254 at the second end 204 of the plate 200, as shown in FIGS. 16, 17, 19, 20, and 22. The base portion 252 may extend away from the plate 200 near the coupling segment 230 on a second side of the plate 200. The base portion 252 may be, for example, a generally uniform thickness. The tapered portion 254 may be tapered, for example, from the top surface 206 to a midpoint between the top surface 206 and the bottom surface 208, from the bottom surface 208 to the midpoint, or from both the top surface 206 and the bottom surface 208 converging at the midpoint. In addition, the tapered portion 254 may be, for example, curved in a superior or inferior direction as it extends away from the base portion 252 of the projection 250. The tapered portion 254 in one embodiment may provide for easier insertion into a patient's bone. The top surface 206 of the first projection 250 may have, for example, a plurality of grooves 266 or a like textured surface to increase surface friction between the plate 200 and the patient's bone and to assist with bone ingrowth into the plate 200 and fixation with adjacent bone surfaces.

The first projection 240 and second projection 250 may extend slightly away from each other forming a channel or space 262 between the projections 240, 250. The size of the channel or space 262 may be selected to enable insertion of the bone plate 200 into a patient's bone without causing the bone to fracture. For example, the first and second projections 240, 250 may extend away from each other at an angle of approximately 5° to 35° and more preferably at an angle of approximately 15° to 25°, although other angles are also contemplated.

The bone plate 200 may also have, for example, a plurality of grooves 264 on at least a portion of the bottom surface 208 of the plate 200. The plurality of grooves 264 may alternatively be another textured surface to increase surface friction between the plate 200 and the patient's bone and to allow for bone ingrowth into the plate 200 or increased contact area to the adjacent bone surface. The bone plate 200 may have, for example, a generally uniform thickness from the first end 202 to the second end 204 with the coupling segment 230 extending above the top surface 206 and the ends 244, 254 being tapered.

Figure 22:
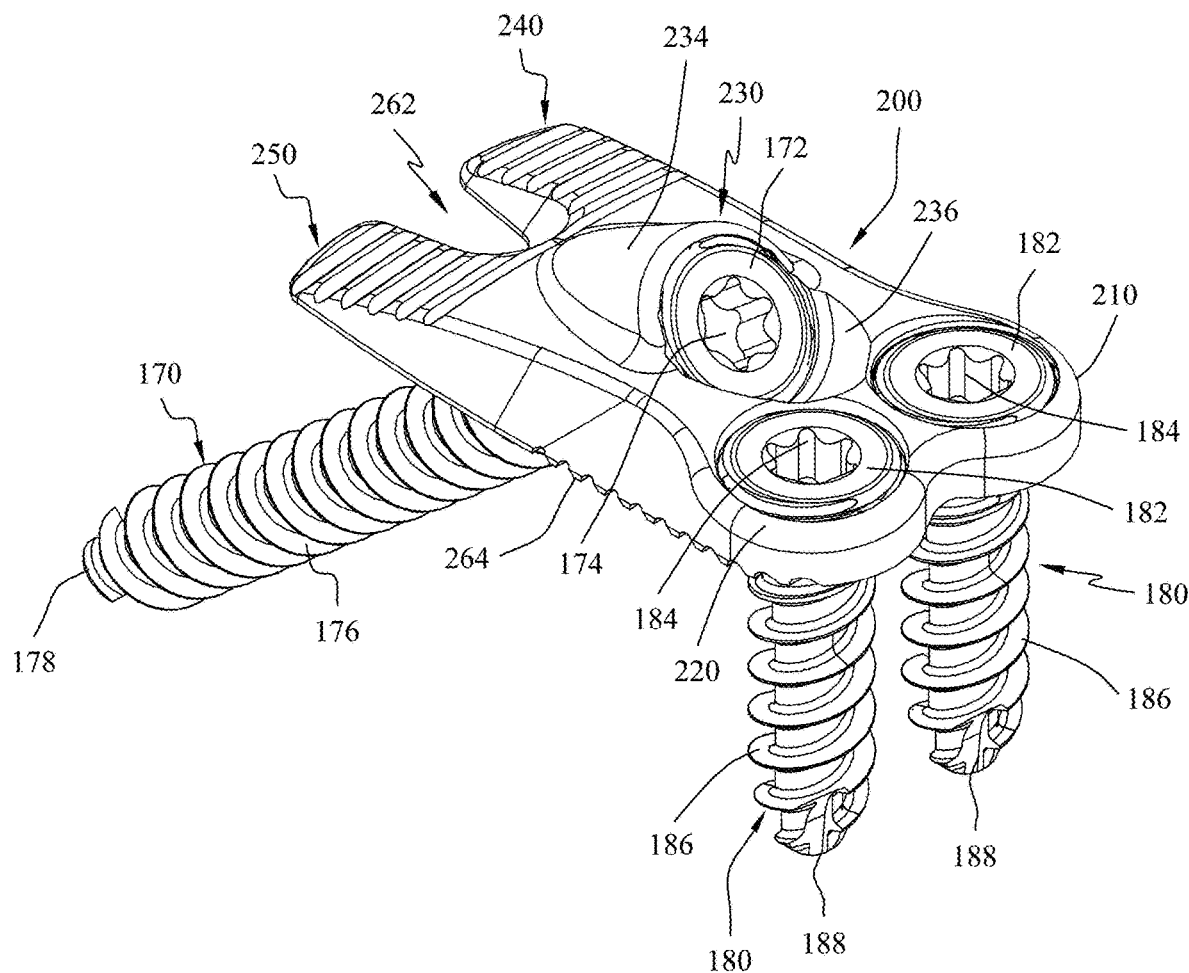
FIG. 22 is an assembled perspective view of the bone plate of FIG. 16 and three fasteners, in accordance with an aspect of the present invention.
Figure 23:
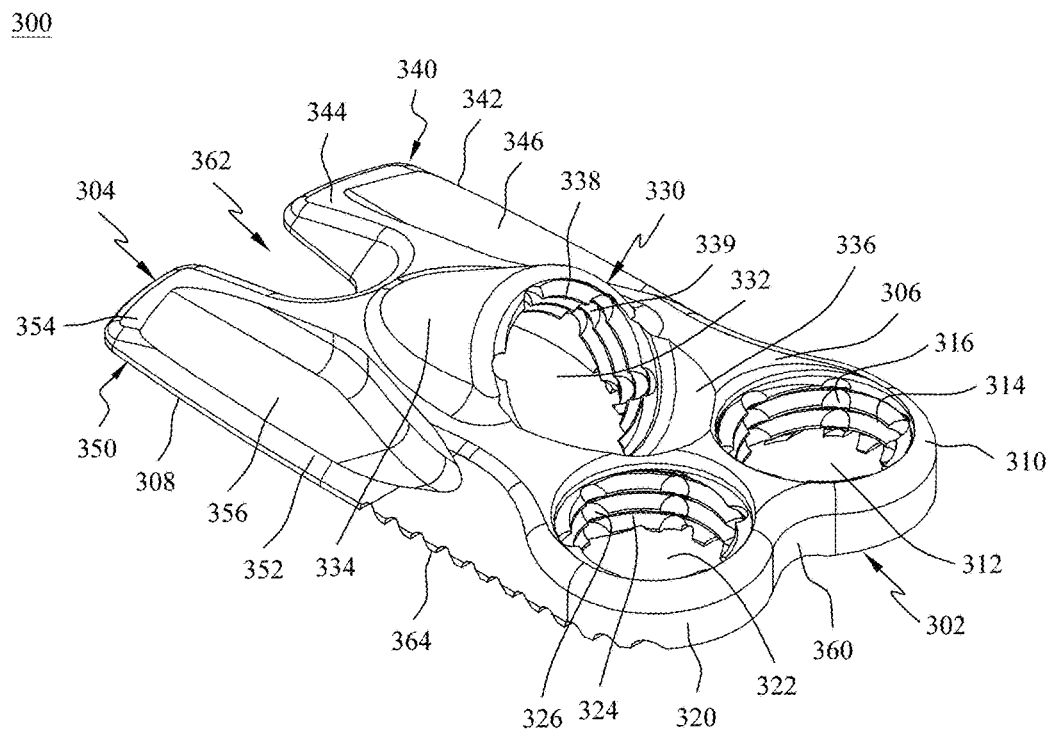
FIG. 23 is a top perspective view of another bone plate, in accordance with an aspect of the present invention.
Figure 24:
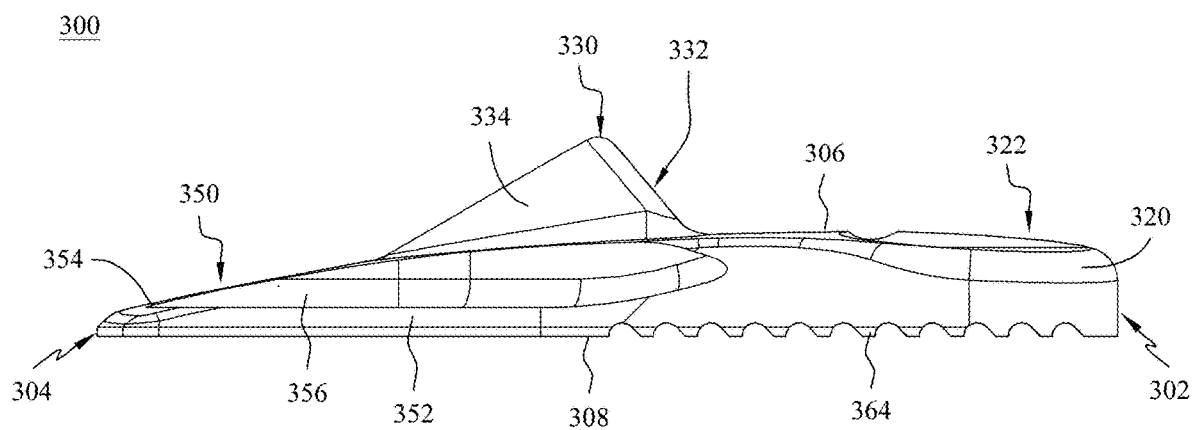
FIG. 24 is a side view of the bone plate of FIG. 23, in accordance with an aspect of the present invention.
Figure 25:
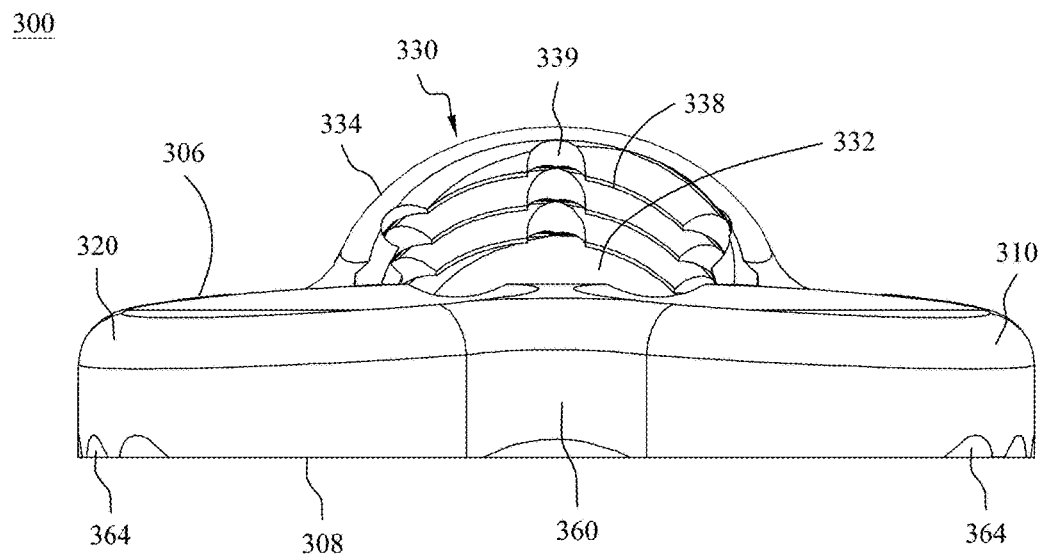
FIG. 25 is a first end view of the bone plate of FIG. 23, in accordance with an aspect of the present invention.
Figure 26:
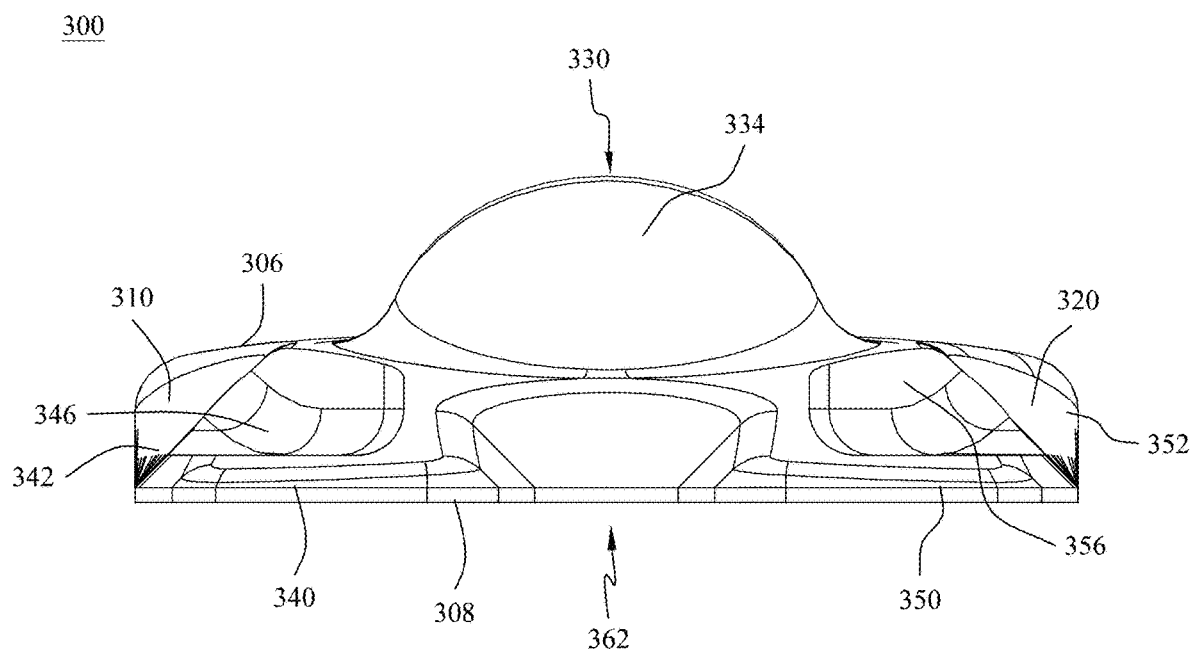
FIG. 26 is a second end view of the bone plate of FIG. 23, in accordance with an aspect of the present invention.

The bone plate 200 may be used with the fasteners 170, 180 to form a bone plate system, as shown in FIG. 22. The fasteners 180 may be inserted through the first lobe 210 and the second lobe 220 until the threads on the head 182 of the fasteners 180 engage the threads 214, 224 in the first and second lobes 210, 220. The fastener 170 may be inserted through the opening 232 in the coupling segment 230 until the threads on the head 172 of the fastener 170 engage the threads 238 in the opening 232.

Another bone plate 300 is shown in FIGS. 23-29. The bone plate 300 may have first end 302, a second end 304 opposite the first end 302, a top surface 306, and a bottom surface 308 opposite the top surface 306. The first end 302 may include, for example, at least one first lobe 310, at least one second lobe 320, and a coupling segment 330. The second end 304 may include, for example, a first projection 340 and a second projection 350. The first and second projections 340, 350 may be, for example, shorter and wider than the first and second projections 140, 150 of the plate 100. The plate 300 may also optionally include a recessed or curved portion 360 positioned between the first and second lobes 310, 320.

As shown in FIGS. 23, 25, and 27-28, the at least one first lobe, fastener opening portion, portion, extension portion, ear, protuberance, enlarged aspect, or tab 310 may be one lobe 310 including an opening 312 with a threaded portion 314 and at least one scallop or cutout 316. The first lobe 310 may be of the type described above with reference to at least one first lobe 110, which will not be described again here for brevity sake. The at least one second lobe, fastener opening portion, portion, extension portion, ear, protuberance, enlarged aspect, or tab 320 may be one lobe 320 including an opening 322 with a threaded portion 324 and at least one scallop or cutout 326. The second lobe 320 may be of the type described above with reference to the at least one second lobe 120, which will not be described again here for brevity sake.

The coupling segment 330, as shown in FIGS. 23-28, may include, for example, an opening 332 with a cover or hood portion 334, an indentation or concavity 336, and a threaded portion 338 with at least one cutout or scallop 339. The coupling segment 330 may be of the type described above with reference to the coupling segment 130, which will not be described again here for brevity sake.

As shown in FIGS. 23 and 26-29, the first projection 340 may include, for example, a base portion 342 and a tapered portion 344 at the second end 304 of the plate 300. The base portion 342 may extend away from the plate 300 near the coupling segment 330 on a first side of the plate 300. The tapered portion 344 may be tapered, for example, from the top surface 306 toward a midpoint between the top surface 306 and the bottom surface 308, from the bottom surface 308 toward the midpoint, or from both the top surface 306 and bottom surface 308 converging at the midpoint. In addition, the tapered portion 344 may be, for example, curved in a superior or inferior direction as it extends away from the base portion 342 of the projection 340. The tapered portion 344 in one embodiment may provide for easier insertion into a patient's bone. The base portion 342 may also have, for example, a recessed area 346 extending into the top surface 306 of the plate 300 from a position adjacent to the coupling segment 330 to the second end 304. The recessed area 346 may be shaped to prevent rotation of the plate 300 once inserted into the patient's bone.

The second projection 350 may include, for example, a base portion 352 and a tapered portion 354 at the second end 304 of the plate 300, as shown in FIGS. 23 and 26-29. The base portion 352 may extend away from the plate 300 near the coupling segment 330 on a second side of the plate 300. The tapered portion 354 may be tapered, for example, from the top surface 306 to a midpoint between the top surface 306 and the bottom surface 308, from the bottom surface 308 to the midpoint, or from both the top surface 306 and the bottom surface 308 converging at the midpoint. In addition, the tapered portion 354 may be, for example, curved in a superior or inferior direction as it extends away from the base portion 352 of the projection 350. The tapered portion 354 in one embodiment may provide for easier insertion into a patient's bone. The base portion 352 may also have, for example, a recessed area 356 extending into the top surface 306 of the plate 300 from a position next to the coupling segment 330 to the second end 304. The recessed area 356 may be shaped to prevent rotation of the plate 300 once inserted into the patient's bone.

The first projection 340 and second projection 350 may extend slightly away from each other creating a space 362 between the projections 340, 350. The size of the space 362 may be selected to enable insertion of the bone plate 300 into a patient's bone without causing the bone to fracture. For example, the first and second projections 340, 350 may extend away from each other at an angle of approximately 5° to 35° and more preferably at an angle of approximately 15° to 25°, although other angles are also contemplated.

The bone plate 300 may also have, for example, a plurality of grooves 364 on at least a portion of the bottom surface 308 of the plate 300. The plurality of grooves 364 may, alternatively, be another textured surface to increase surface friction between the plate 300 and the patient's bone and to allow for bone ingrowth into the plate 300 and fixation with adjacent bone surfaces. The bone plate 300 may have, for example, a generally uniform thickness from the first end 302 to the second end 304 with the coupling segment 330 extending above the top surface 306 and the ends 344, 354 being tapered.

Figure 29:
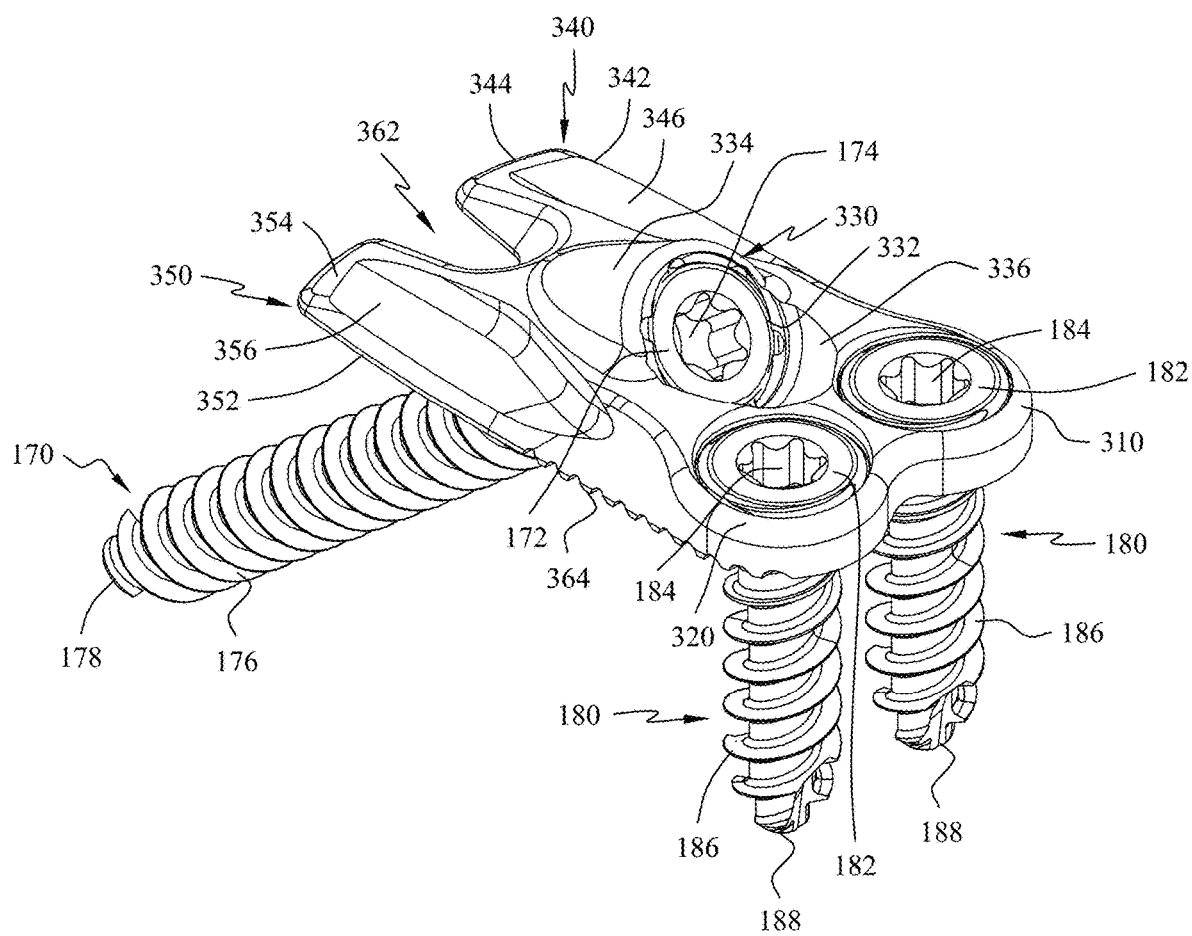
FIG. 29 is a perspective view of the bone plate of FIG. 23 with three fasteners, in accordance with an aspect of the present invention.
Figure 30:
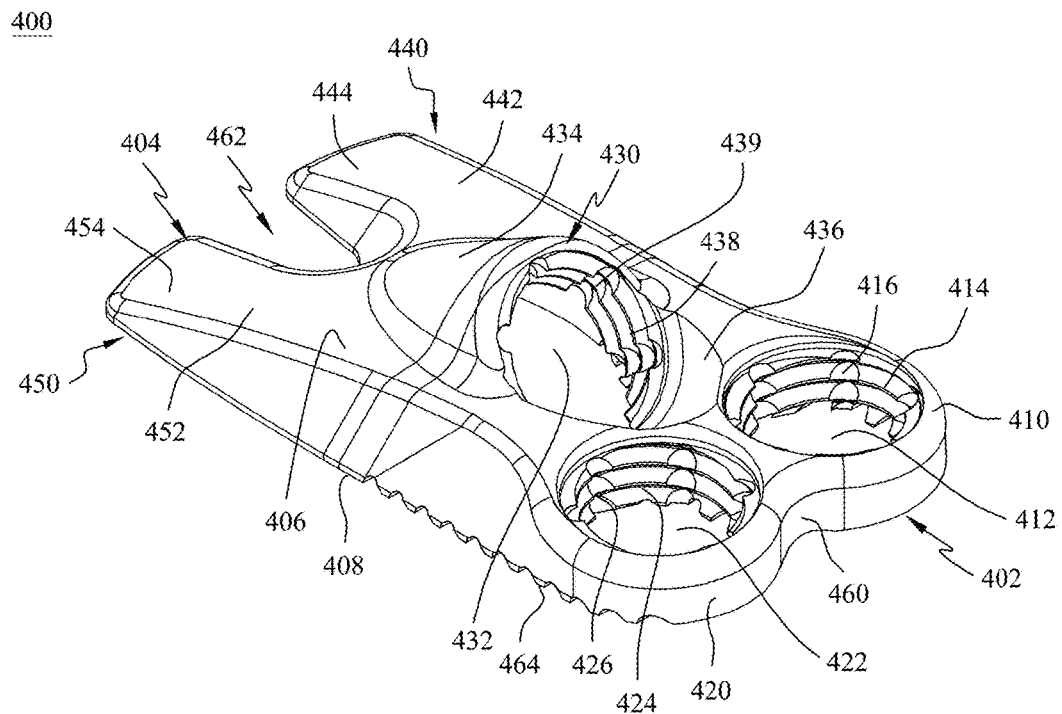
FIG. 30 is a top perspective view of yet another bone plate, in accordance with an aspect of the present invention.
Figure 31:
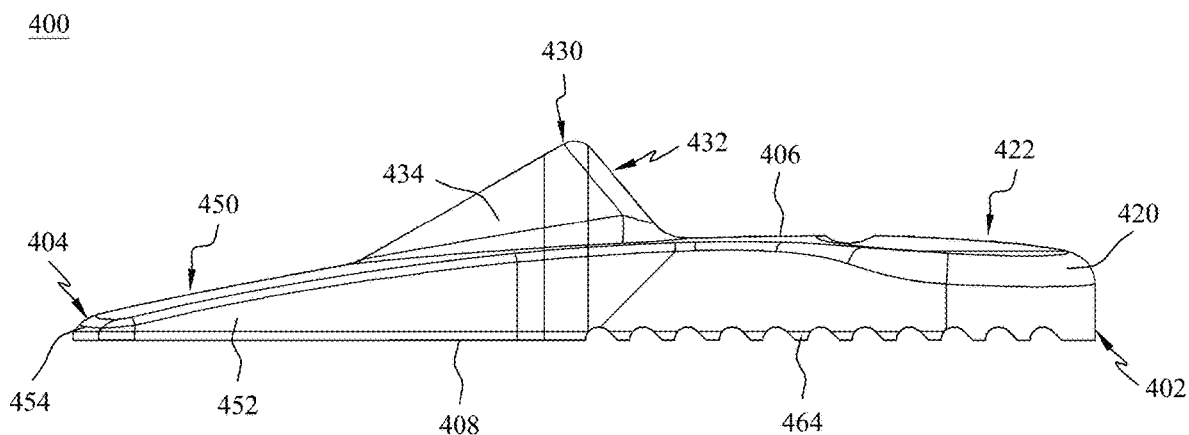
FIG. 31 is a side view of the bone plate of FIG. 30, in accordance with an aspect of the present invention.
Figure 32:
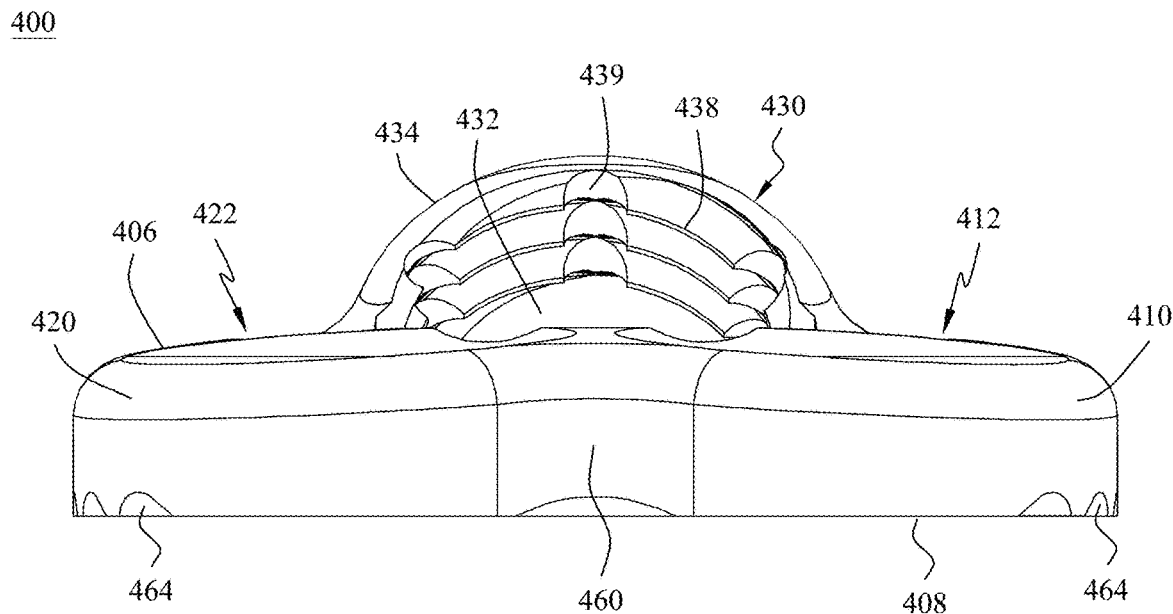
FIG. 32 is a first end view of the bone plate of FIG. 30, in accordance with an aspect of the present invention.
Figure 33:
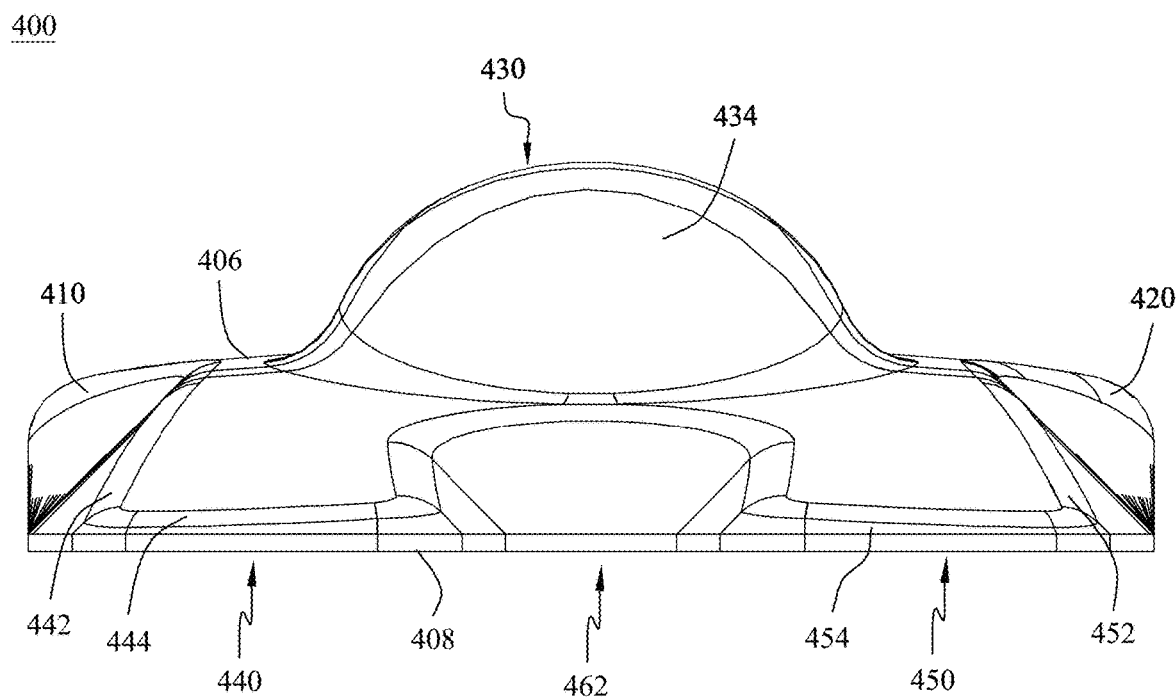
FIG. 33 is a second end view of the bone plate of FIG. 30, in accordance with an aspect of the present invention.
Figure 34:
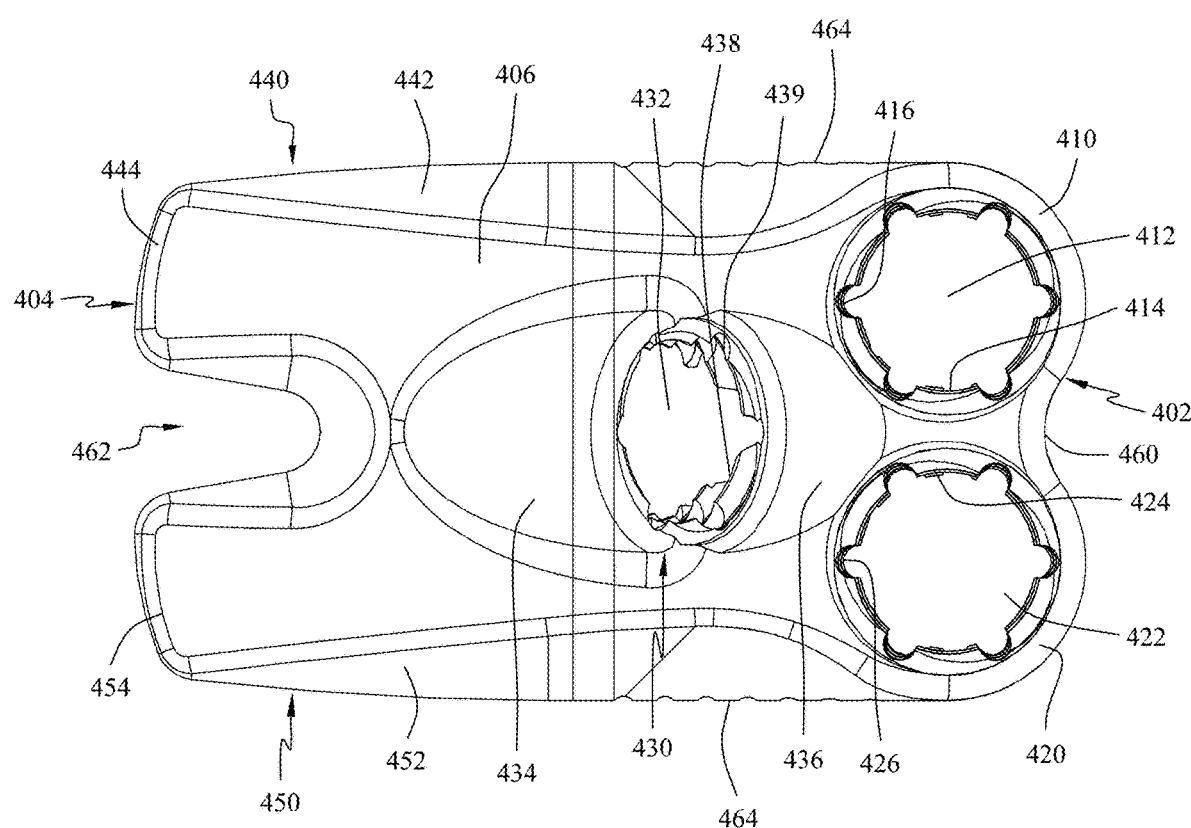
FIG. 34 is a top view of the bone plate of FIG. 30, in accordance with an aspect of the present invention.
Figure 35:
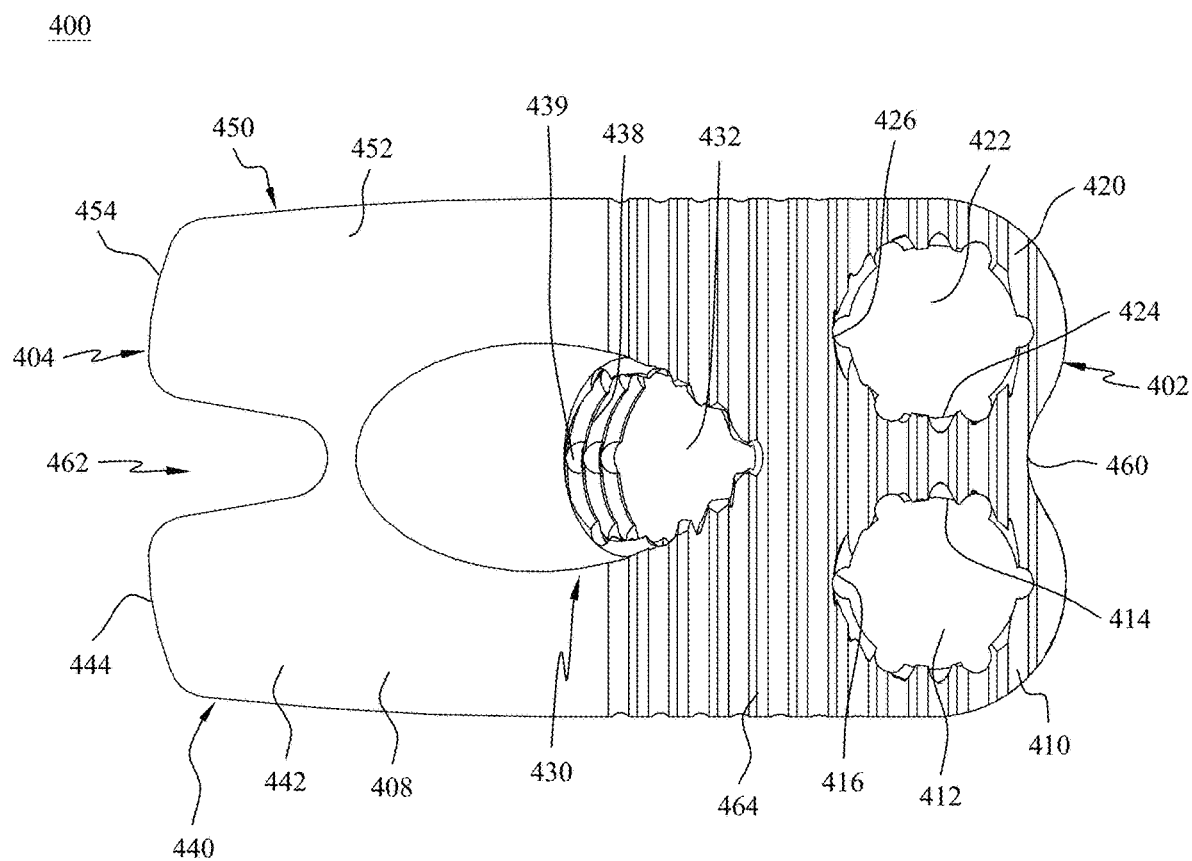
FIG. 35 is a bottom view of the bone plate of FIG. 30, in accordance with an aspect of the present invention.

The bone plate 300 may be used with the fasteners 170, 180 to form a bone plate system, as shown in FIG. 29. The fasteners 180 may be inserted through the first lobe 310 and the second lobe 320. As the fasteners 180 are inserted the threads on the heads 182 of the fasteners 180 engage with the threads 314, 324 in the openings 312, 322 of the lobes 310, 320 to lock the fasteners 180 to the plate 300. The fastener 170 may be inserted through the opening 332 in the coupling segment 330. As the fastener 170 is inserted the threads on the head 172 of the fastener 170 engages the threads 338 in the opening 332 of the coupling segment 330 to lock the fastener 170 to the plate 300.

Another bone plate 400 is shown in FIGS. 30-40. The bone plate 400 may have first end 402, a second end 404 opposite the first end 402, a top surface 406, and a bottom surface 408 opposite the top surface 406. The first end 402 may include, for example, at least one first lobe 410, at least one second lobe 420, and a coupling segment 430. The second end 404 may include, for example, a first projection 440 and a second projection 450. The first and second projections 440, 450 may be, for example, shorter and wider than the first and second projections 140, 150 of the plate 100. In addition, the first and second lobes 410, 420 may be positioned closer together that the first and second lobes 110, 120 of plate 100. In addition, the first and second lobes 410, 420 may be positioned in front of the opening 432 of the coupling segment 430. The plate 400 may also optionally include a recessed or curved portion 460 positioned between the first and second lobes 410, 420.

As shown in FIGS. 30, 32, 34, and 35, the at least one first lobe, fastener opening portion, portion, extension portion, ear, protuberance, enlarged aspect, or tab 410 may be one lobe 410 including an opening 412 with a threaded portion 414 and at least one scallop or cutout 416. The first lobe 410 may be of the type described above with reference to at least one first lobe 110, which will not be described again here for brevity sake. The at least one second lobe, fastener opening portion, portion, extension portion, ear, protuberance, enlarged aspect, or tab 420 may be one lobe 420 including an opening 422 with a threaded portion 424 and at least one scallop or cutout 426. The second lobe 420 may be of the type described above with reference to the at least one second lobe 120, which will not be described again here for brevity sake.

The coupling segment 430, as shown in FIGS. 30-36, may include, for example, an opening 432 with a cover or hood portion 434, an indentation or concavity 436, and a threaded portion 438 with at least one cutout or scallop 439. The coupling segment 430 may be of the type described above with reference to the coupling segment 130, which will not be described again here for brevity sake.

As shown in FIGS. 30 and 33-36, the first projection 440 may include, for example, a base portion 442 and a tapered portion 444 at the second end 404 of the plate 400. The base portion 442 may extend away from the plate 400 near the coupling segment 430 on a first side of the plate 400. The tapered portion 444 may be tapered, for example, from the top surface 406 toward a midpoint between the top surface 406 and the bottom surface 408, from the bottom surface 408 toward the midpoint, or from both the top surface 406 and bottom surface 408 converging at the midpoint. In addition, the tapered portion 444 may be, for example, curved in a superior or inferior direction as it extends away from the base portion 442 of the projection 440. The tapered portion 444 in one embodiment may provide for easier insertion into a patient's bone.

The second projection 450 may include, for example, a base portion 452 and a tapered portion 454 at the second end 404 of the plate 400, as shown in FIGS. 30, 31, and 33-36. The base portion 452 may extend away from the plate 400 near the coupling segment 430 on a second side of the plate 400. The tapered portion 454 may be tapered, for example, from the top surface 406 to a midpoint between the top surface 406 and the bottom surface 408, from the bottom surface 408 to the midpoint, or from both the top surface 406 and the bottom surface 408 converging at the midpoint. In addition, the tapered portion 454 may be, for example, curved in a superior or inferior direction as it extends away from the base portion 452 of the projection 450. The tapered portion 454 in one embodiment may provide for easier insertion into a patient's bone.

The first projection 440 and second projection 450 may extend slightly away from each other forming a channel or space 462 between the projections 440, 450. The size of the space or channel 462 may be selected to enable insertion of the bone plate 400 into a patient's bone without causing the bone to fracture. For example, the first and second projections 440, 450 may extend away from each other at an angle of approximately 5° to 35° and more preferably at an angle of approximately 15° to 25°, although other angles are also contemplated.

The bone plate 400 may also have, for example, a plurality of grooves 464 on at least a portion of the bottom surface 408 of the plate 400. The plurality of grooves 464 may, alternatively, be another textured surface to allow for bone ingrowth into the plate 400 and fixation with adjacent bone surfaces. The bone plate 400 may have, for example, a generally uniform thickness from the first end 402 to the second end 404 with the coupling segment 430 extending above the top surface 406 and the ends 444, 454 being tapered.

Figure 36:
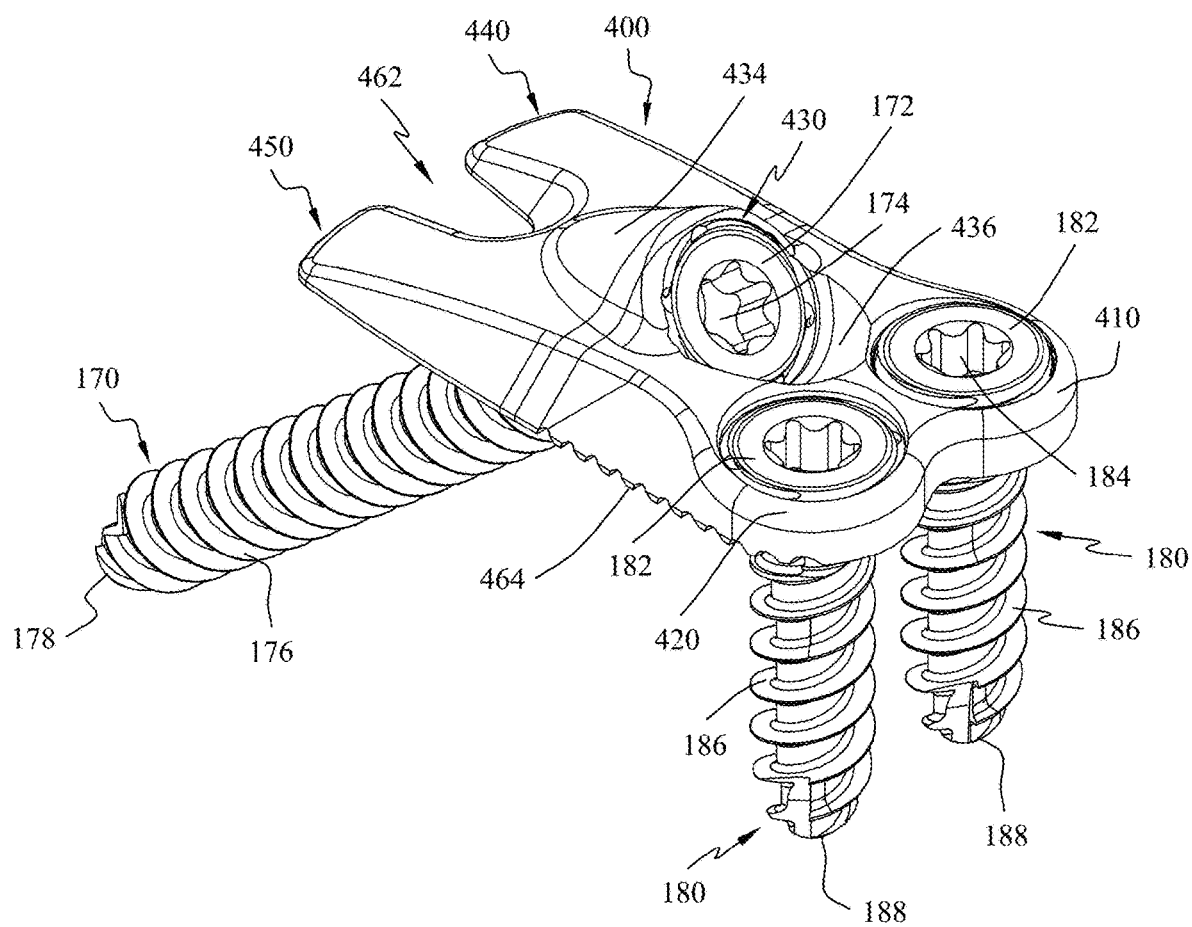
FIG. 36 is a perspective view of the bone plate of FIG. 30 with three fasteners, in accordance with an aspect of the present invention.

The bone plate 400 may be used with the fasteners 170, 180 to form a bone plate system, as shown in FIG. 36. The fasteners 180 may be inserted through the first lobe 410 and the second lobe 420 to engage the threads 414, 424. The fastener 170 may be inserted through the opening 432 in the coupling segment 430 to engage the threads 438.

Figure 37:
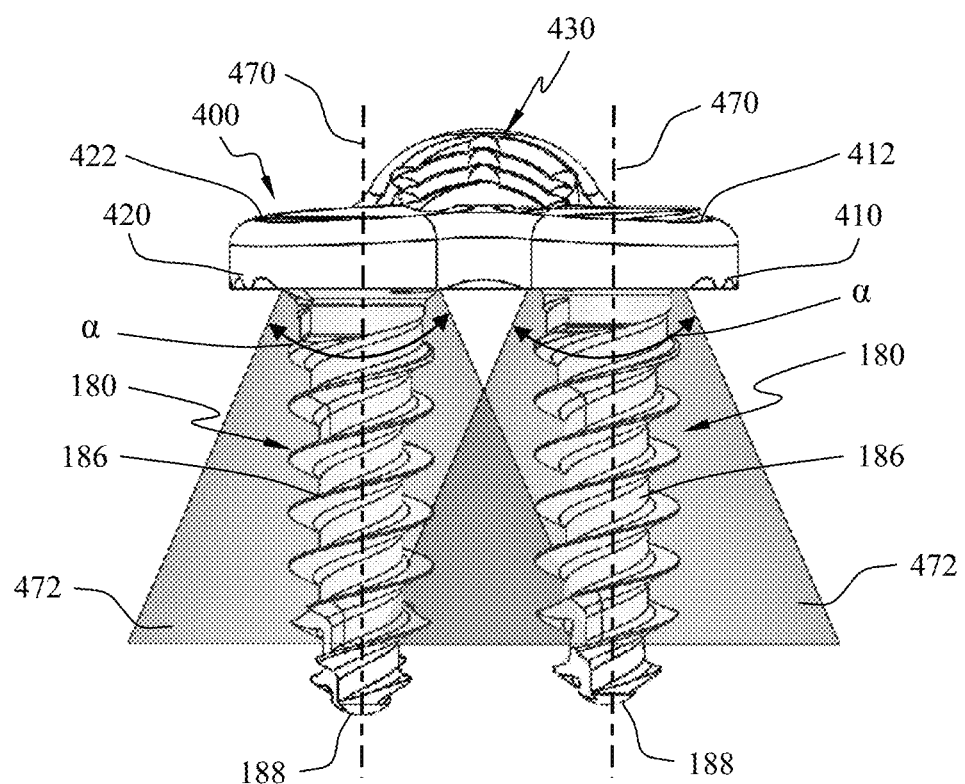
FIG. 37 is a first end view of the bone plate of FIG. 30 with two fasteners showing the insertion angles for the two fasteners, in accordance with an aspect of the present invention.
Figure 38:
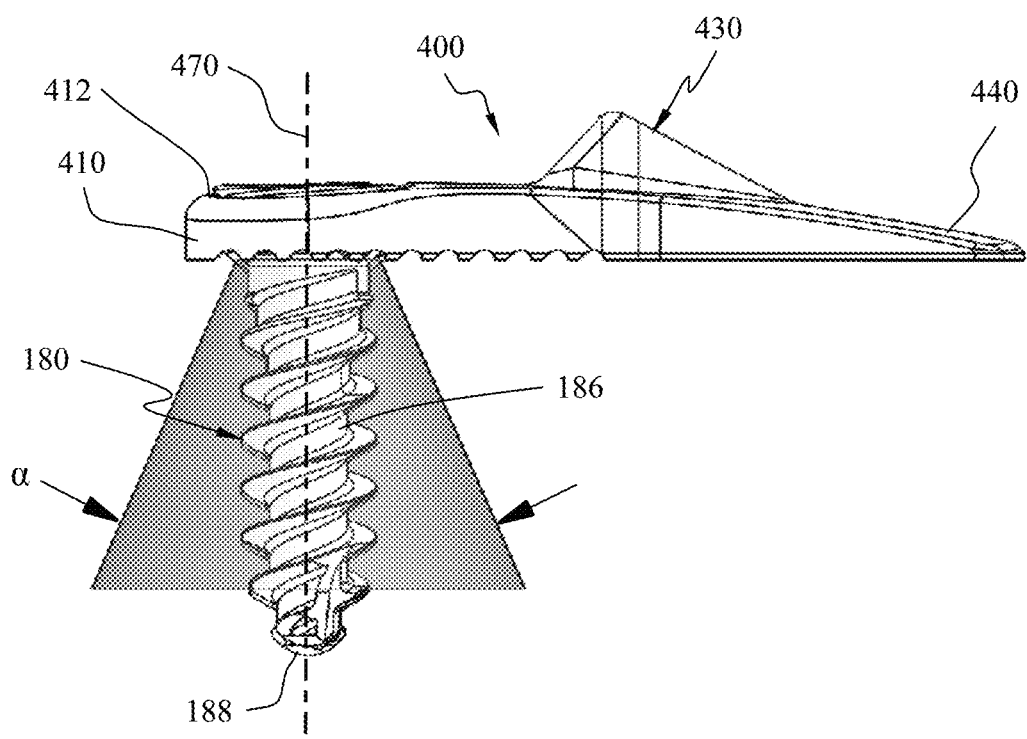
FIG. 38 is another side view of the bone plate and two fasteners of FIG. 37 showing the insertion angles for the two fasteners, in accordance with an aspect of the present invention.

FIGS. 37 and 38 show the possible angles of insertion for the fasteners 180 through openings 412, 422. The openings 412, 422 may have an included angle α centered on opening axis 470. The included angle α of the openings 412, 422 may be, for example, approximately 30°. The included angle α enables the fasteners 180 to be inserted through openings 412, 422 in an off-axis position within the shaded region 472. The shaded region 472, as shown in FIG. 37, illustrates the insertion angles from the opening axis 470 in a medial-lateral direction. The shaded region 472, as shown in FIG. 38, illustrates the insertion angles from the opening axis 470 in a proximal-distal direction. For example, if the included angle α is approximately 30°, then the insertion angles may be 15° from the opening axis 470 in every direction forming a conical area where the fasteners 180 may be inserted. The fasteners 180 may be, for example, locking fasteners to secure the fasteners 180 at any of the inserted angles within the plate 400, as discussed above.

Referring now to FIGS. 39 and 40, the possible angles of insertion for the fastener 170 through opening 432 are shown. The opening 432 may have an included angle β centered on opening axis 480. As the opening 432 is angled relative to the top surface of the plate 400, the opening axis 480 is also angled relative to the top surface of the plate 400. The included angle β of the opening 432 may be, for example, approximately 30°. The included angle β enables the fastener 170 to be inserted through the opening 432 in an off-axis position within the shaded region 482. The shaded region 482, as shown in FIG. 39, illustrates the insertion angles from the opening axis 480 viewed from a proximal end of the plate. The shaded region 482, as shown in FIG. 40, illustrates the insertion angles from the opening axis 480 viewed from a medial or lateral side of the plate 400. For example, if the included angle β is approximately 30°, then the insertion angles may be 15° from the opening axis 480 in every direction forming a conical area where the fastener 170 may be inserted. The fastener 170 may be, for example, a locking fastener to secure the fastener 170 at any of the inserted angles within the plate 400, as discussed above.

The openings 112, 122, 132, 212, 222, 232, 312, 322, 332 of plates 100, 200, 300 may be as described above with reference to openings 412, 422, 432 of plate 400, which will not be described again here for brevity sake. Thus, fasteners 170, 180 may also be inserted through the openings 112, 122, 132, 212, 222, 232, 312, 322, 332 in the bone plates 100, 200, and 300 in an off-axis position within the region created by the included angles α, β.

Another bone plate 700 is shown in FIGS. 46-51. The bone plate 700 may have first end 702, a second end 704 opposite the first end 702, a top surface 706, and a bottom surface 708 opposite the top surface 706. The first end 702 may include, for example, at least one first lobe 710, at least one second lobe 720, and a coupling segment 730. The second end 704 may include, for example, a first projection 740 and a second projection 750. The first and second projections 740, 750 may be, for example, shorter and wider than the first and second projections 140, 150 of the plate 100. In addition, the first and second lobes 710, 720 may be positioned farther apart than the first and second lobes 110, 120 of plate 100. In addition, the first and second lobes 710, 720 may be positioned to slightly overlap the opening 732 of the coupling segment 730. The plate 700 may also optionally include a recessed or curved portion 760 positioned between the first and second lobes 710, 720.

As shown in FIGS. 46-49, the at least one first lobe, fastener opening portion, portion, extension portion, ear, protuberance, enlarged aspect, or tab 710 may be one lobe 710 including an opening 712 with a threaded portion 714 and at least one scallop or cutout 716. The first lobe 710 may be of the type described above with reference to at least one first lobe 110, 410, which will not be described again here for brevity sake. The at least one second lobe, fastener opening portion, portion, extension portion, ear, protuberance, enlarged aspect, or tab 720 may be one lobe 720 including an opening 722 with a threaded portion 724 and at least one scallop or cutout 726. The second lobe 720 may be of the type described above with reference to the at least one second lobe 120, 420, which will not be described again here for brevity sake.

The coupling segment 730, as shown in FIGS. 46-49, may include, for example, an opening 732 with a cover or hood portion 734, an indentation or concavity 736, and a threaded portion 738 with at least one cutout or scallop 739. The coupling segment 730 may be of the type described above with reference to the coupling segment 130, 430 which will not be described again here for brevity sake. The coupling segment 730 may also extend between the first projection 740 and the second projection 750 such that the end of the coupling segment 730 is adjacent to the ends of the first and second projections 740, 750. The position of the coupling segment 730 in relation to the first and second projections 740, 750 enables the end of each of the coupling segment 730, the first projection 740 and the second projection 750 to be inserted into the patient's bone.

As shown in FIGS. 46-48 and 50, the first projection 740 may include, for example, a base portion 742 and a tapered portion 744 at the second end 704 of the plate 700. The base portion 742 may extend away from the plate 700 adjacent to the coupling segment 730 on a first side of the plate 700. The tapered portion 744 may be tapered, for example, from the top surface 706 toward a midpoint between the top surface 706 and the bottom surface 708, from the bottom surface 708 toward the midpoint, or from both the top surface 406 and bottom surface 708 converging at the midpoint. In addition, the tapered portion 744 may be, for example, curved in a superior or inferior direction as it extends away from the base portion 742 of the projection 740. The tapered portion 744 in one embodiment may provide for easier insertion into a patient's bone.

The second projection 750 may include, for example, a base portion 752 and a tapered portion 754 at the second end 704 of the plate 700, as shown in FIGS. 46-48 and 50-51. The base portion 752 may extend away from the plate 700 adjacent to the coupling segment 730 on a second side of the plate 700. The tapered portion 754 may be tapered, for example, from the top surface 706 to a midpoint between the top surface 706 and the bottom surface 708, from the bottom surface 708 to the midpoint, or from both the top surface 706 and the bottom surface 708 converging at the midpoint. In addition, the tapered portion 754 may be, for example, curved in a superior or inferior direction as it extends away from the base portion 752 of the projection 750. The tapered portion 754 in one embodiment may provide for easier insertion into a patient's bone.

The first projection 740 and second projection 750 may be spaced apart from the coupling segment 730 forming a channel or space 762 between each of the projections 740, 750 and the coupling segment 730. The size of the space or channel 762 and first and second projections 740, 750 may be selected to enable insertion of the bone plate 700 into a patient's bone without causing the bone to fracture. The width of each of the first and second projections 740, 750 in a medial-lateral direction may be, for example, approximately 3.5 mm to 6.5 mm, and more preferably, approximately 5 mm to 5.2 mm.

The bone plate 700 may also have, for example, a textured surface, a plurality of grooves, or the like on at least a portion of the bottom surface 708 of the plate 700 to allow for bone ingrowth into the plate 700 and fixation with adjacent bone surfaces. The bone plate 700 may have, for example, a generally uniform thickness from the first end 702 to the second end 704 with the coupling segment 730 extending above the top surface 706 and the ends 744, 754 being tapered.

The bone plate 700 may be used with the fasteners 170, 180 to form a bone plate system. The fasteners 180 may be inserted through the first lobe 710 and the second lobe 720 to engage the threads 714, 724. The fastener 170 may be inserted through the opening 732 in the coupling segment 730 to engage the threads 738.

The possible angles of insertion for the fasteners 180 through openings 712, 722 may be as described above with reference to FIGS. 37 and 38, which will not be described again here for brevity sake. The possible angles of insertion for the fastener 170 through opening 732 may be as described above with reference to FIGS. 39 and 40, which will not be described again here for brevity sake. The fasteners 170, 180 may be, for example, locking fasteners to secure the fasteners 170, 180 at any of the inserted angles within the plate 700, as discussed above.

Figure 45:
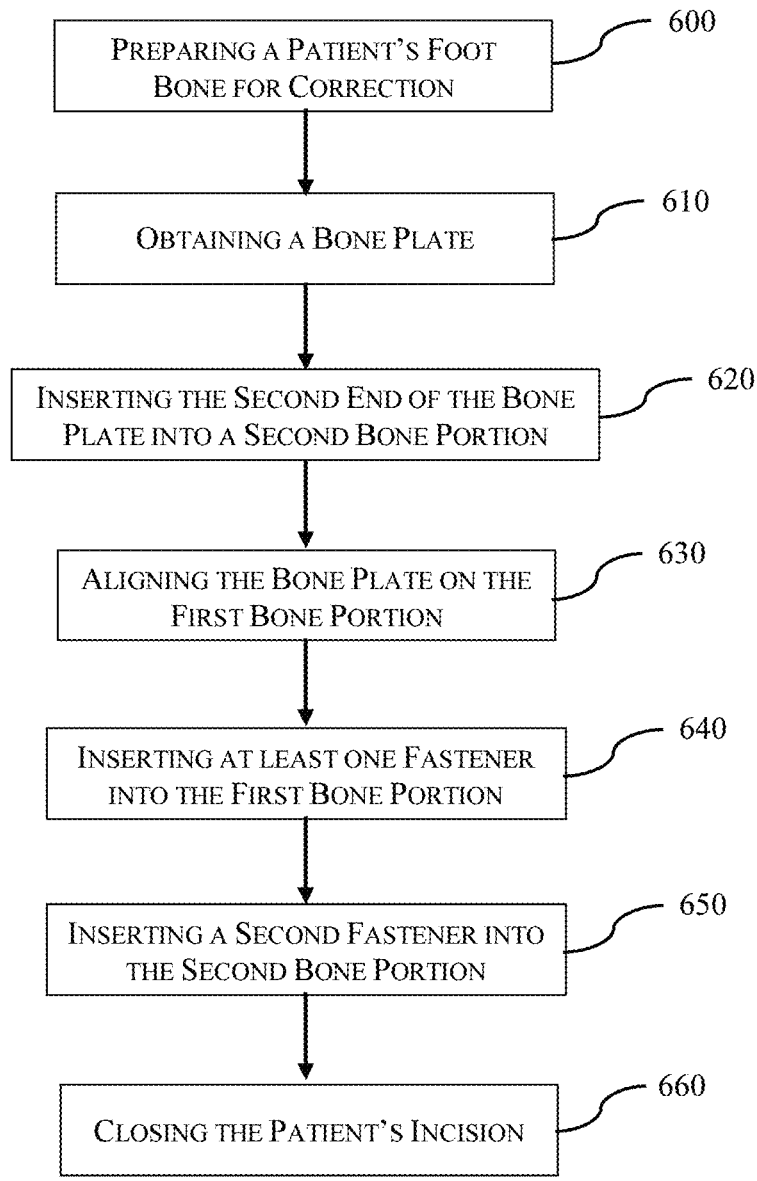
FIG. 45 depicts one embodiment of a method for using a bone plate system of FIG. 9, 22, 29, or 36, in accordance with an aspect of the present invention.
Figure 46:
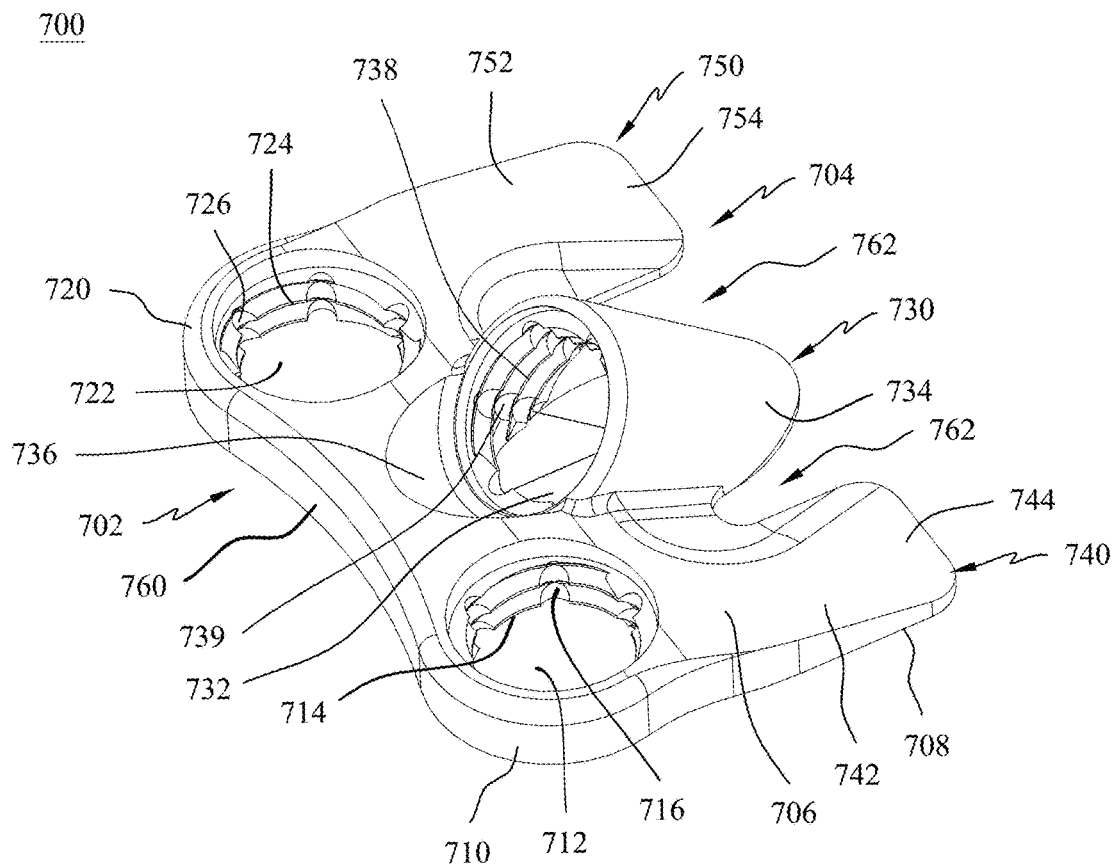
FIG. 46 is a top perspective view of yet another bone plate, in accordance with an aspect of the present invention.
Figure 47:
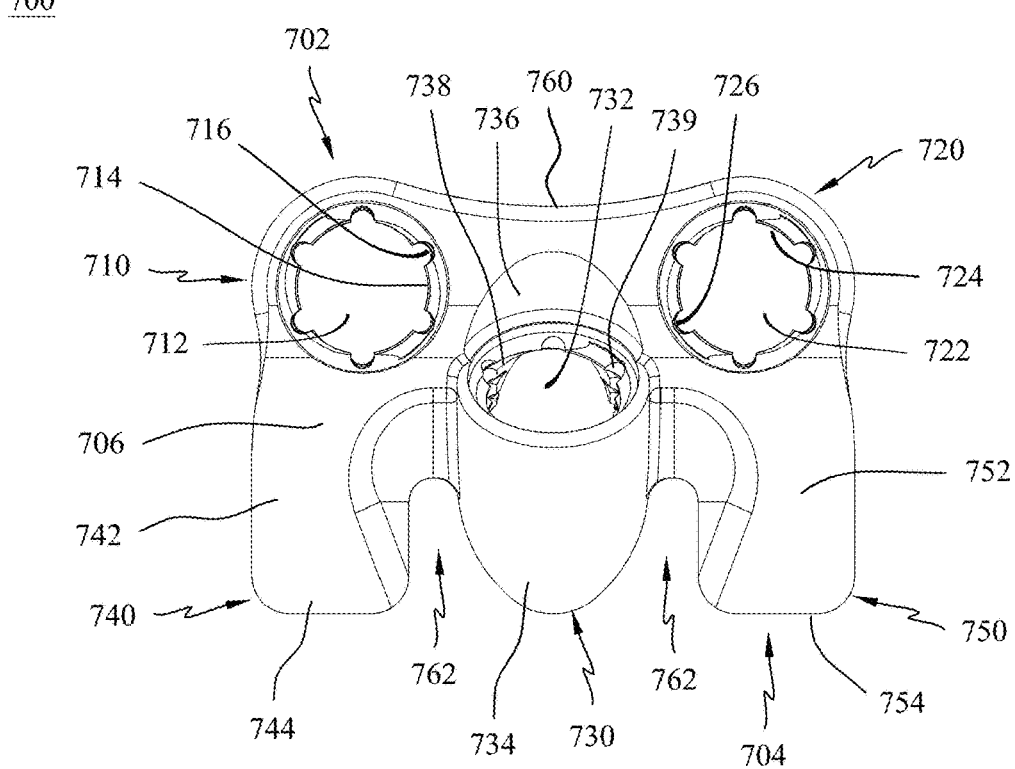
FIG. 47 is a top view of the bone plate of FIG. 46, in accordance with an aspect of the present invention.
Figure 48:
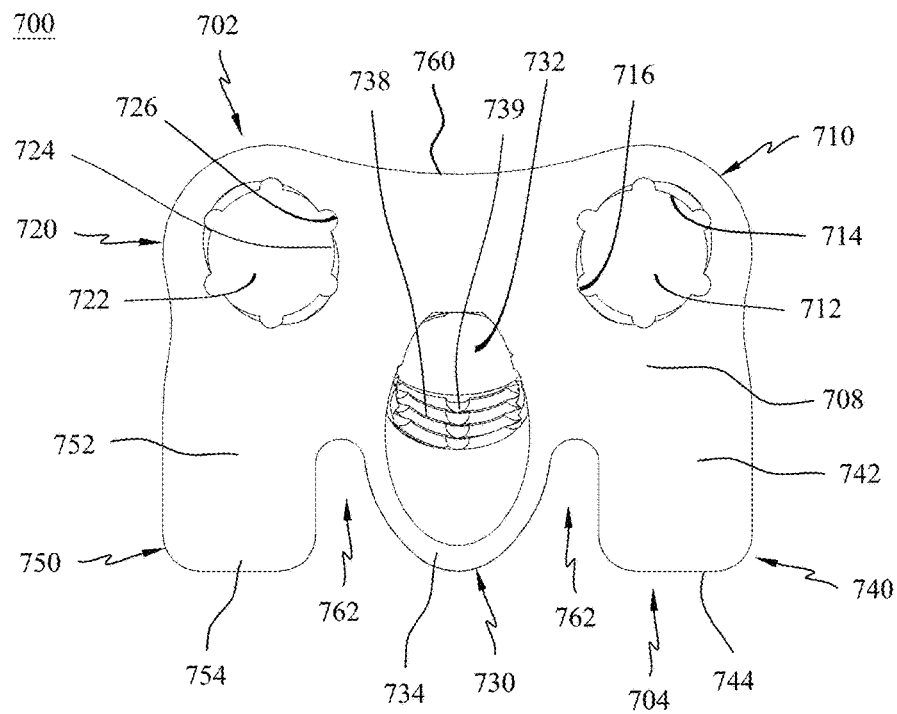
FIG. 48 is a bottom view of the bone plate of FIG. 46, in accordance with an aspect of the present invention.
Figure 49:
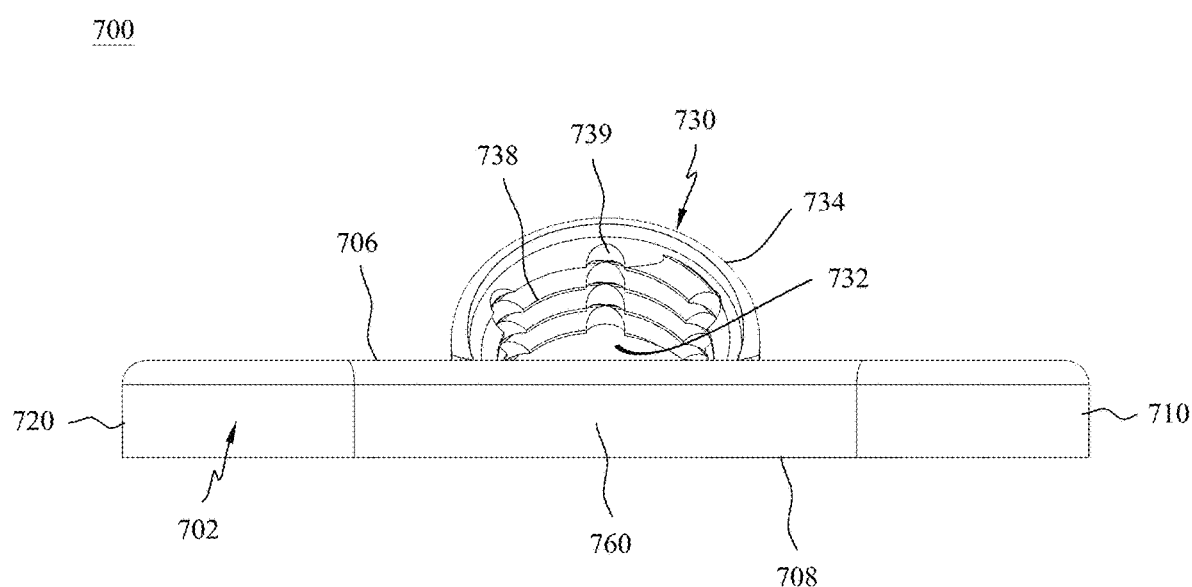
FIG. 49 is a first end view of the bone plate of FIG. 46, in accordance with an aspect of the present invention.
Figure 50:
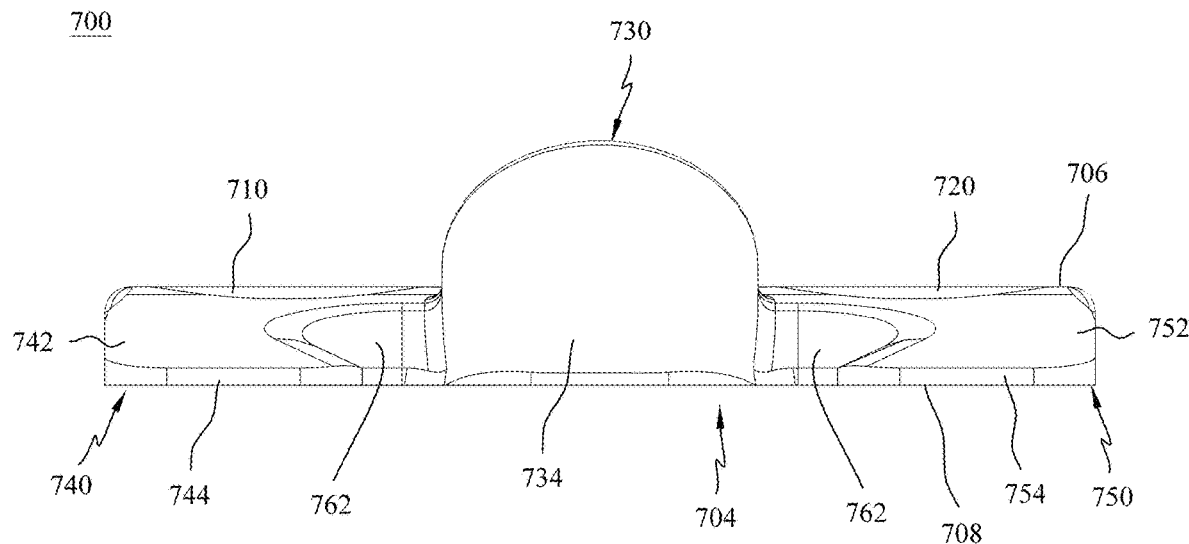
FIG. 50 is a second end view of the bone plate of FIG. 46, in accordance with an aspect of the present invention.
Figure 51:
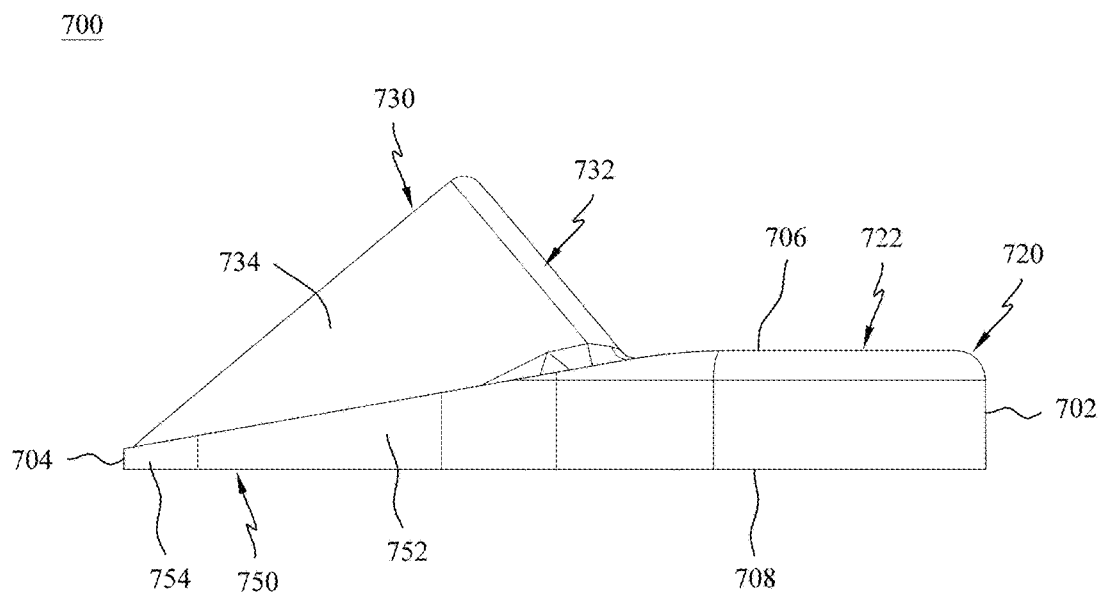
FIG. 51 is a side view of the bone plate of FIG. 46, in accordance with an aspect of the present invention.

A method for using a bone plate system is shown in FIG. 45. The method may include preparing a patient's foot bone for correction 600 and obtaining a bone plate system 610. Next, the method may include inserting the second end of the bone plate into a second bone portion 620. The method may also include aligning the first end of the bone plate with the first bone portion 630. Then, the method may include inserting at least one fastener through the first end of the bone plate and into the first bone portion 640 and inserting a fastener through the second end of the bone plate and into the second bone portion 650. Finally, the method may include closing the patient's incision 660.

Figure 27:
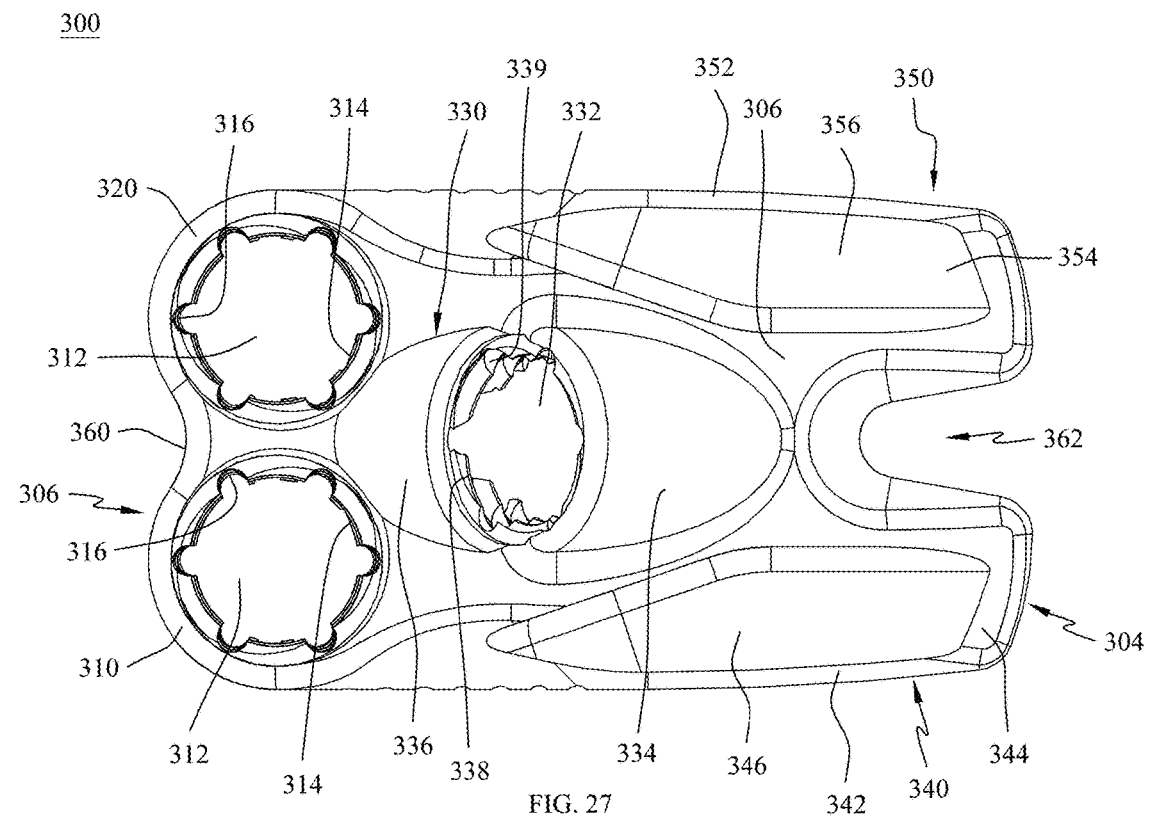
FIG. 27 is a top view of the bone plate of FIG. 23, in accordance with an aspect of the present invention.
Figure 28:
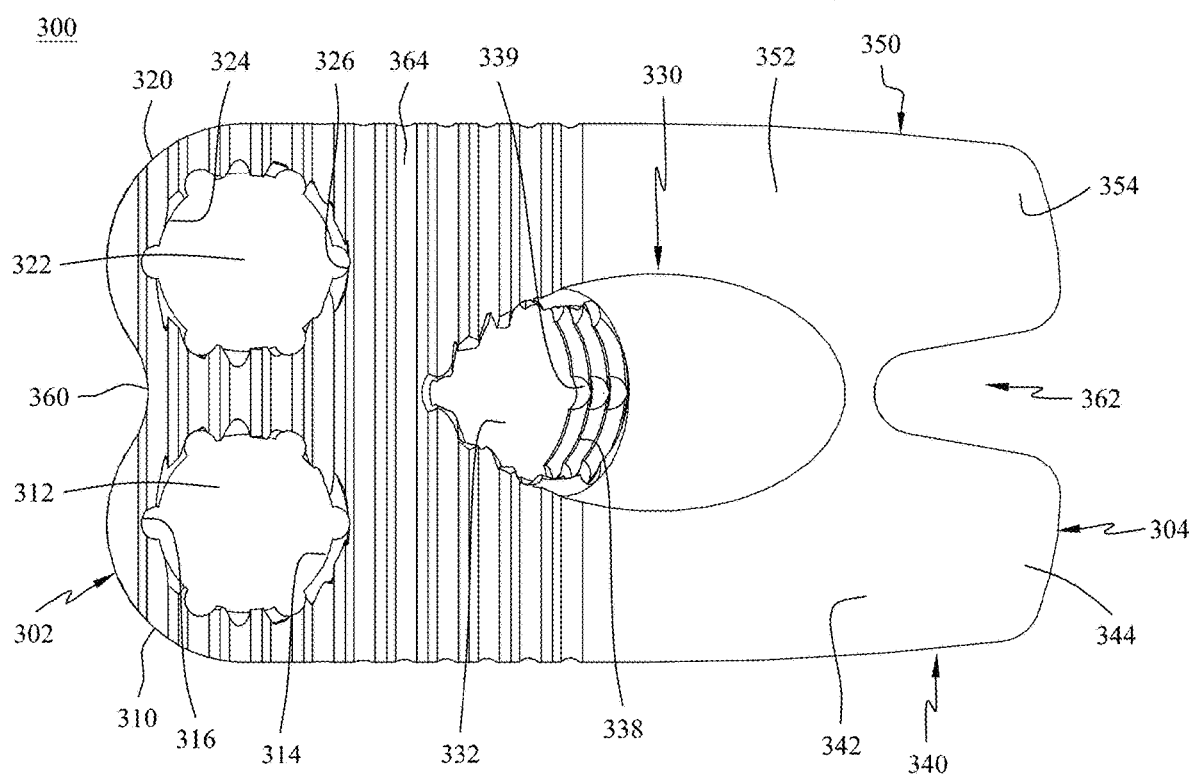
FIG. 28 is a bottom view of the bone plate of FIG. 23, in accordance with an aspect of the present invention.
Figure 41:
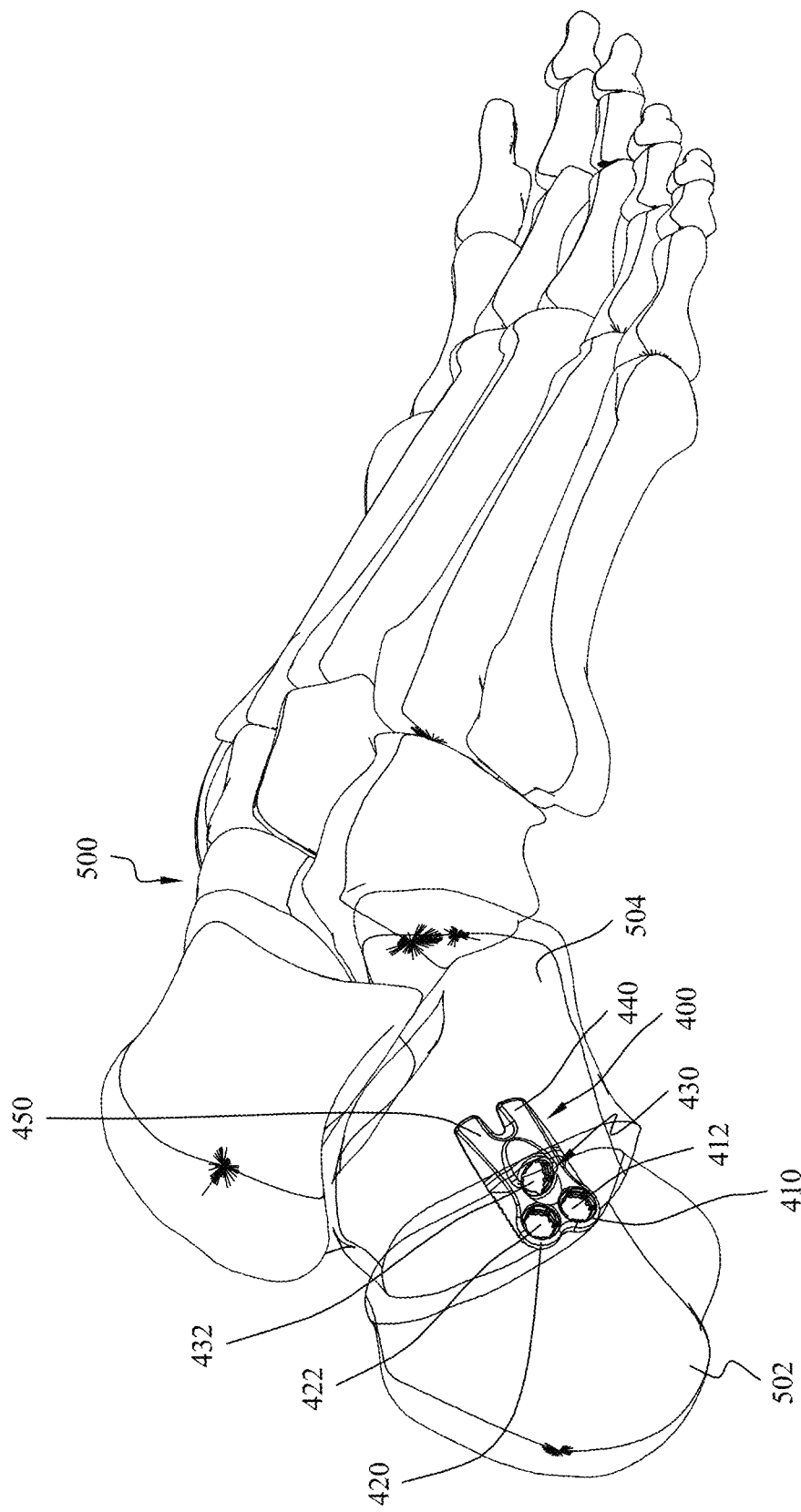
FIG. 41 is a transparent perspective side view of the bones of a patient's foot showing a bone plate aligned with a first portion of the calcaneus and inserted into a second portion of the calcaneus, in accordance with an aspect of the present invention.
Figure 42:
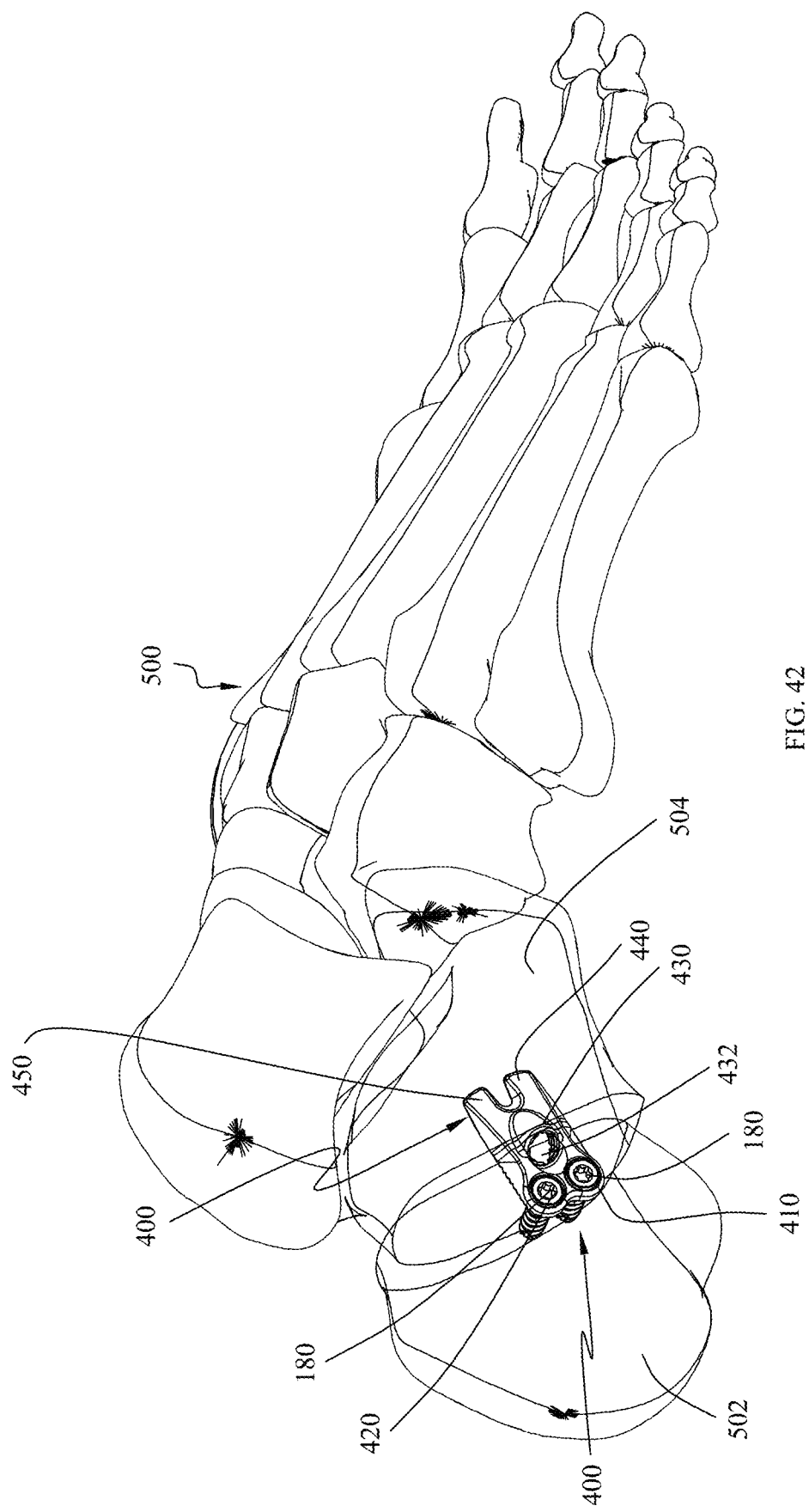
FIG. 42 is a transparent perspective view of the foot of FIG. 41 with two fasteners inserted through the bone plate and into the first portion of the calcaneus, in accordance with an aspect of the present invention.
Figure 43:
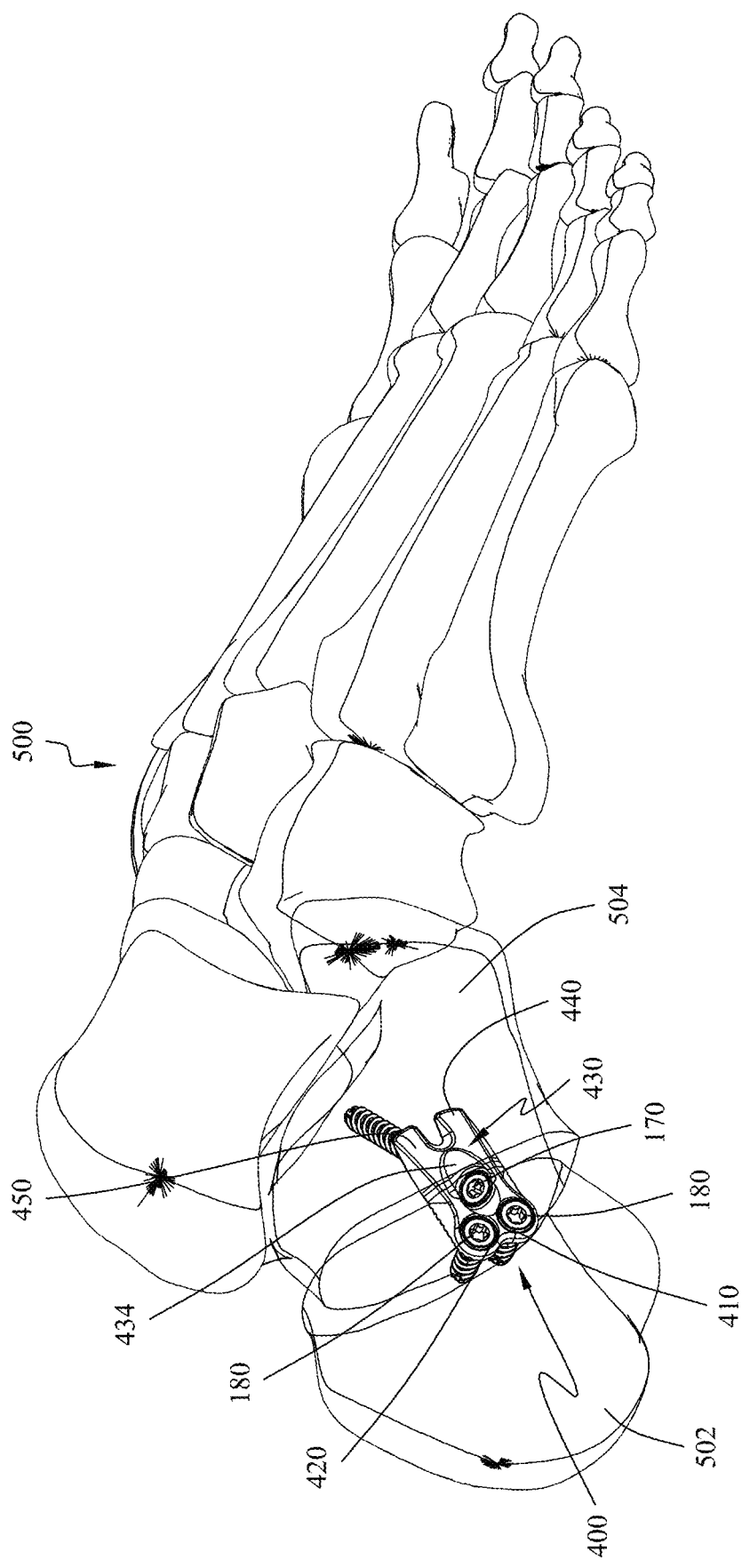
FIG. 43 is a transparent perspective view of the foot of FIG. 41 with a third fastener inserted though the bone plate and into the second portion of the calcaneus, in accordance with an aspect of the present invention.
Figure 44:
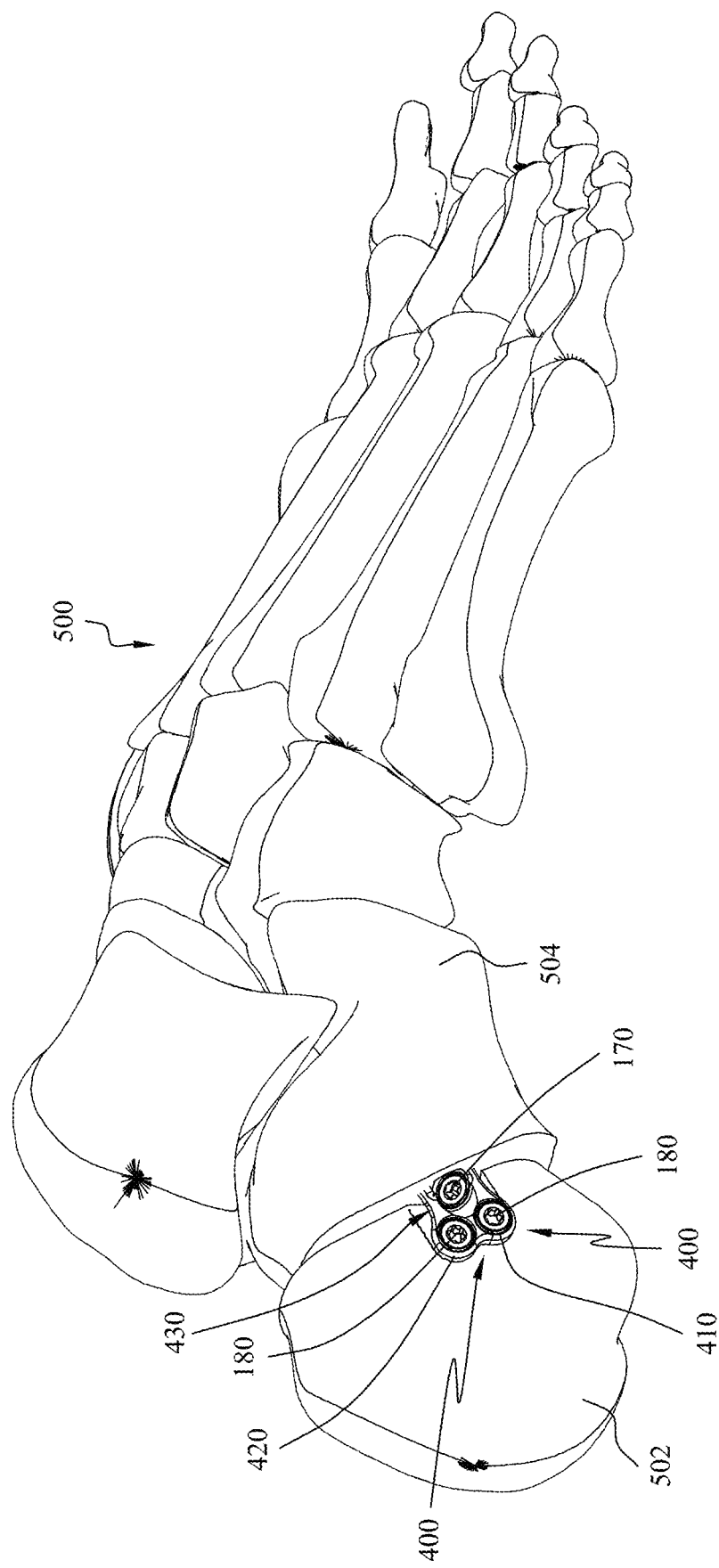
FIG. 44 is a perspective view of the foot and bone plate of FIG. 43 with a solid calcaneus, in accordance with an aspect of the present invention.

The method of FIG. 45 may be described in greater detail with reference to FIGS. 41-44. A patient's foot 500 is shown in FIG. 41 with the bone plate 400 inserted into a bone. The foot 500 may include a bone with a first portion 502 and a second 504. The first and second portions 502, 504 may be formed by a fracture or cut by a surgeon to correct a deformity. The bone may be, for example, a calcaneus bone. As shown in FIG. 27, the second end 404 of the plate 400 may be inserted into the second bone portion 504 and aligned with the first bone portion 502. Once the plate 400 is in the desired position with respect to the first and second bone portions 502, 504, at least one fastener 180 may be inserted into the at least one first and second lobes 410, 420, as shown in FIG. 42. The fasteners 180 may be inserted through the openings 412, 422 in the lobes 410, 420 and into the first bone portion 502. Next, a fastener 170 may be inserted through the coupling segment 430 and into the second bone portion 504, as shown in FIG. 43. The fastener 170 may be inserted at an angle into the second bone portion 504. The fastener 170 may be, for example, longer than the fasteners 180. After each of the fasteners 170, 180 are inserted into the first and second bone portions 502, 504, the surgeon may close the patient's incision. As shown in FIG. 44, the first bone portion 502 may be positioned offset from the second bone portion 504. Although only described in detail for bone plate 400, the method for using a bone plate system as shown and described in FIGS. 41-45 may also be used with bone plates 100, 200, 300 and 700.

As may be recognized by those of ordinary skill in the art based on the teachings herein, numerous changes and modifications may be made to the above-described and other embodiments of the present invention without departing from the scope of the invention. The projections, coupling segment, and other components of the device and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 1-15, FIGS. 16-22, FIGS. 23-29, FIGS. 30-40, and FIGS. 46-51 may all be used interchangeably and in alternative combinations as would be modified or altered by one of skill in the art. Accordingly, this detailed description of the currently-preferred embodiments is to be taken in an illustrative, as opposed to limiting of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A bone plate, comprising:
   at least one protuberance at a first end;
   a first projection at a second end;
   a second projection at the second end adjacent to the first projection, wherein the first and second projections extend at least one of away from and toward one another at a first angle and define a channel therebetween, wherein each of the first and second projections have a base portion and a tapered portion at the second end of the bone plate, and wherein the tapered portions are tapered from at least one of a top surface and a bottom surface through the thickness of the bone plate; and
   a coupling segment positioned between the first projection and second projection, the coupling segment comprising:
      an opening extending through the bone plate at an oblique angle relative to a bottom surface of the bone plate; and
      a cover at least partially surrounding the opening, wherein the cover extends from the coupling segment to a position between the first and second projections and into the channel adjacent to the tapered portion at the second end of the bone plate.

2. The bone plate of claim 1, wherein the first end is a proximal end and the second end is a distal end, wherein the base portions extend from a position distal to the at least one protuberance to the tapered portions and wherein the base portion has a generally uniform thickness.

3. The bone plate of claim 1, wherein the at least one protuberance comprises:
   a first protuberance; and
   a second protuberance positioned adjacent to the first protuberance.

4. The bone plate of claim 3, wherein a portion of the coupling segment is positioned between the first protuberance and the second protuberance.

5. The bone plate of claim 1, wherein the at least one protuberance comprises:
   an opening extending through the bone plate; and
   a threaded portion in the opening.

6. The bone plate of claim 5, wherein the at least one protuberance further comprises:
   at least one cutout positioned along the threaded portion, wherein the at least one cutout extends entirely through the threaded portion from a top surface of the bone plate to the bottom surface of the bone plate.

7. The bone plate of claim 1, wherein the opening of the coupling segment comprises:
   a threaded portion in the opening.

8. The bone plate of claim 7, wherein the coupling segment further comprises:
   a concavity adjacent to the opening and positioned between the opening and the at least one protuberance, wherein the concavity is recessed into a top surface of the bone plate adjacent to a portion of a top surface of the cover.

9. The bone plate of claim 8, wherein the coupling segment further comprises:
   at least one cutout positioned along the threaded portion, wherein the at least one cutout extends entirely through the threaded portion parallel with the opening of the coupling segment.

10. The bone plate of claim 3, wherein the cover extends from a first position between the first protuberance and the second protuberance to a second position between the first projection and the second projection, and wherein the cover extends at an oblique angle from the bottom surface of the bone plate to a first end of the cover positioned on a top side of the bone plate.

11. The bone plate of claim 1, wherein the first angle is between 15 degrees and 45 degrees.

12. The bone plate of claim 1, wherein the first and second projections each further comprise an interior linear portion, wherein the interior linear portions each include an upper edge, and wherein at least the upper edges of the interior linear portions extend at least one of away from and toward one another at the first angle and define the channel therebetween.

13. A bone plate system, comprising:
   a bone plate, comprising:
      at least one tab at a first end;
      a second end with a first projection and a second projection adjacent to the first projection, wherein interior surfaces of the first and second projections extend at least one of away from and toward one another at a first angle and define a channel therebetween, wherein each of the first and second projections have a base portion and a tapered portion at the second end of the bone plate, and wherein the tapered portions are tapered from at least one of a top surface and a bottom surface through the thickness of the bone plate; and
      a coupling segment positioned adjacent to the at least one tab and between the first projection and the second projection, wherein the coupling segment comprises:
         an opening extending through the bone plate at an oblique angle relative to a bottom surface of the bone plate; and
         a cover at least partially surrounding the opening, and wherein the cover extends from the coupling segment to a position between the first and second projections and into the channel adjacent to the tapered portion at the second end of the bone plate; and
   at least one fastener, comprising:
      at least one first fastener for coupling to the at least one tab; and
      a second fastener for coupling to the coupling segment.

14. The bone plate system of claim 13, wherein the at least one tab comprises:
   a first tab; and
   a second tab positioned adjacent to the first tab.

15. The bone plate system of claim 13, wherein the at least one tab comprises:
   an opening extending through the bone plate;
   a threaded portion in the opening; and
   at least one cutout positioned along the threaded portion and forming gaps in the threaded portion that extend from a top surface of the bone plate to the bottom surface.

16. The bone plate system of claim 13, wherein the coupling segment comprises:
   a threaded portion in the opening;
   at least one cutout positioned along the threaded portion; and
   a concavity adjacent to the opening and positioned between the opening and the at least one tab.

17. The bone plate system of claim 14, wherein the coupling segment is positioned between at least a portion of the first tab and the second tab and extends between the first projection and the second projection.

18. A method for using the bone plate of claim 1, comprising:
   cutting an incision over a patient's bone;
   preparing the patient's bone;
   selecting the bone plate;
   inserting the second end of the bone plate into a second bone portion;
   aligning the bone plate on a first bone portion;
   inserting at least one fastener through the bone plate and into the first bone portion;
   inserting a fastener through the bone plate and into the second bone portion; and
   closing the incision.

19. A bone plate, comprising:
   at least one protuberance at a first end;
   a first projection at a second end;
   a second projection at the second end adjacent to the first projection, wherein the first and second projections comprise an interior linear portion, wherein the interior linear portions each include an upper edge, and wherein at least the upper edges of the interior linear portions extend at least one of away from and toward one another at a first angle and define a channel therebetween; and
   a coupling segment positioned between the first projection and second projection, the coupling segment comprising:
      an opening extending through the bone plate at an oblique angle relative to a bottom surface of the bone plate; and
      a cover at least partially surrounding the opening, and wherein the cover extends from the coupling segment to a position between the first and second projections and into the channel adjacent to a tapered portion at the second end of the bone plate.

* * * * *